United States Patent
Wu et al.

(10) Patent No.: US 8,445,454 B2
(45) Date of Patent: May 21, 2013

(54) USE ON MINICIRCLE VECTORS FOR CARDIAC GENE THERAPY

(75) Inventors: Joseph Wu, Palo Alto, CA (US); Mark A. Kay, Los Altos, CA (US); Mei Huang, Menlo Park, CA (US); Zhi-Ying Chen, Foster City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/925,483

(22) Filed: Oct. 22, 2010

(65) Prior Publication Data

US 2011/0118333 A1 May 19, 2011

Related U.S. Application Data

(60) Provisional application No. 61/279,676, filed on Oct. 23, 2009, provisional application No. 61/338,467, filed on Feb. 18, 2010.

(51) Int. Cl.
*A61K 48/00* (2006.01)
*C07H 21/04* (2006.01)
*C07H 21/02* (2006.01)
*C12N 15/63* (2006.01)

(52) U.S. Cl.
USPC ...... 514/44; 536/23.1; 536/24.31; 536/24.33; 536/24.5; 435/320.1

(58) Field of Classification Search
None
See application file for complete search history.

(56) References Cited

PUBLICATIONS

Scherer et al. (Nat. Biotechnol., 2003, 21(12), pp. 1457-1465).*
Chan; et al., "Coordinate Regulation of the Oxygen-Dependent Degradation Domains of Hypoxia-Inducible Factor 1alpha", Molecular and Cellular Biology (2005): 25(15):6415-6426.
Chan; et al., "Role of Prolyl Hydroxylation in Oncogenically Stabilized Hypoxia-inducible Factor-1alpha", The Journal of Biological Chemistry (2002), 277(42):40112-40117.
Darquet: et al., "A new DNA vehicle for nonviral gene delivery: supercoiled minicircle", Gene Therapy (1997), 4:1341-1349.
Darquet; et al., "Minicircle: an improved DNA molecule for in vitro and in vivo gene transfer", Gene Therapy (1999), 6:209-218.
Hirota; et al., "Regulation of hypoxia-inducible factor 1 by prolyl and asparaginyl hydroxylases", Biochemical and Biophysical Research Communications (2005), 338:610-616.
Huang; et al., "Novel Minicircle Vector for Gene Therapy in Murine Myocardial Infarction", Circulation (2009), 120(11 Suppl):S230-S237.
Huang; et al., "Short Hairpin RNA Interference Therapy for Ischemic Heart Disease", Circulation (2008), 118(14 Suppl):S226-233.
Nataranjan; et al., "Hypoxia Inducible Factor-1 Activation by Prolyl 4-Hydroxylase-2 Gene Silencing Attenuates Myocardial Ischemia Reperfusion Injury", Circulation Research (2006), 98(1):133-140.

* cited by examiner

*Primary Examiner* — Amy Bowman
(74) *Attorney, Agent, or Firm* — Bozicevic, Field & Francis LLP; Pamela J. Sherwood

(57) ABSTRACT

Compositions and methods are provided for the treatment of an ischemic cardiovascular condition by providing a patient with a novel non-viral minicircle DNA vector comprising polynucleotide sequences that potentiate HIF-1 activity, including RNAi or antisense agents selective for proteins involved in HIF1 inactivation.

12 Claims, 14 Drawing Sheets
(11 of 14 Drawing Sheet(s) Filed in Color)

SEQUENCE LISTING

```
<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: synthetic primer

<400> SEQUENCE: 1
ccgaattcat gaactttctg ctgtcttggg                                        30

<210> SEQ ID NO 2
<211> LENGTH: 27
<212> TYPE: DNA
<213> ORGANISM: Artificial Sequence
<220> FEATURE:
<223> OTHER INFORMATION: synthetic primer

<400> SEQUENCE: 2
aaaagcggcc gctcattcat tcatcac                                           27

<210> SEQ ID NO 3
<211> LENGTH: 426
<212> TYPE: PRT
<213> ORGANISM: H. sapiens

<400> SEQUENCE: 3

Met Ala Asn Asp Ser Gly Gly Pro Gly Gly Pro Ser Pro Ser Glu Arg
 1               5                  10                  15

Asp Arg Gln Tyr Cys Glu Leu Cys Gly Lys Met Glu Asn Leu Leu Arg
            20                  25                  30

Cys Ser Arg Cys Arg Ser Ser Phe Tyr Cys Cys Lys Glu His Gln Arg
        35                  40                  45

Gln Asp Trp Lys Lys His Lys Leu Val Cys Gln Gly Ser Glu Gly Ala
    50                  55                  60

Leu Gly His Gly Val Gly Pro His Gln His Ser Gly Pro Ala Pro Pro
65                  70                  75                  80

Ala Ala Val Pro Pro Pro Arg Ala Gly Ala Arg Glu Pro Arg Lys Ala
                85                  90                  95

Ala Ala Arg Arg Asp Asn Ala Ser Gly Asp Ala Ala Lys Gly Lys Val
            100                 105                 110

Lys Ala Lys Pro Pro Ala Asp Pro Ala Ala Ala Ser Pro Cys Arg
        115                 120                 125

Ala Ala Ala Gly Gly Gln Gly Ser Ala Val Ala Ala Glu Ala Glu Pro
    130                 135                 140

Gly Lys Glu Glu Pro Pro Ala Arg Ser Ser Leu Phe Gln Glu Lys Ala
145                 150                 155                 160

Asn Leu Tyr Pro Pro Ser Asn Thr Pro Gly Asp Ala Leu Ser Pro Gly
                165                 170                 175

Gly Gly Leu Arg Pro Asn Gly Gln Thr Lys Pro Leu Pro Ala Leu Lys
            180                 185                 190

Leu Ala Leu Glu Tyr Ile Val Pro Cys Met Asn Lys His Gly Ile Cys
```

```
                195                 200                 205
Val Val Asp Asp Phe Leu Gly Lys Glu Thr Gly Gln Gln Ile Gly Asp
    210                 215                 220

Glu Val Arg Ala Leu His Asp Thr Gly Lys Phe Thr Asp Gly Gln Leu
225                 230                 235                 240

Val Ser Gln Lys Ser Asp Ser Lys Asp Ile Arg Gly Asp Lys Ile
                245                 250                 255

Thr Trp Ile Glu Gly Lys Glu Pro Gly Cys Glu Thr Ile Gly Leu Leu
            260                 265                 270

Met Ser Ser Met Asp Asp Leu Ile Arg His Cys Asn Gly Lys Leu Gly
        275                 280                 285

Ser Tyr Lys Ile Asn Gly Arg Thr Lys Ala Met Val Ala Cys Tyr Pro
    290                 295                 300

Gly Asn Gly Thr Gly Tyr Val Arg His Val Asp Asn Pro Asn Gly Asp
305                 310                 315                 320

Gly Arg Cys Val Thr Cys Ile Tyr Tyr Leu Asn Lys Asp Trp Asp Ala
                325                 330                 335

Lys Val Ser Gly Gly Ile Leu Arg Ile Phe Pro Glu Gly Lys Ala Gln
            340                 345                 350

Phe Ala Asp Ile Glu Pro Lys Phe Asp Arg Leu Leu Phe Phe Trp Ser
        355                 360                 365

Asp Arg Arg Asn Pro His Glu Val Gln Pro Ala Tyr Ala Thr Arg Tyr
    370                 375                 380

Ala Ile Thr Val Trp Tyr Phe Asp Ala Asp Glu Arg Ala Arg Ala Lys
385                 390                 395                 400

Val Lys Tyr Leu Thr Gly Glu Lys Gly Val Arg Val Glu Leu Asn Lys
                405                 410                 415

Pro Ser Asp Ser Val Gly Lys Asp Val Phe
            420                 425

<210> SEQ ID NO 4
<211> LENGTH: 7102
<212> TYPE: DNA
<213> ORGANISM: H. sapiens

<400> SEQUENCE: 4
ttaggggcag aaaaacattt gtaataatta atggctttga gagacacaag gctttgtttg      60
ccccagagta ttagttaacc cacctagtgc tcctaatcat acaatattaa ggattgggag     120
ggacattcat tgcctcactc tctatttgtt tcaccttctg taaaattggt agaataatag     180
tacccacttc atagcattgt atgatgatta aattggttaa tattttaaa atgcttagaa      240 cacagattgg gcacataaca gcaagcacca catgtgttta agataaat tccttttgtgt     300 tgccttccgt taaagtttaa ataagtaaat aaataaataa atacttgcat gacattttga     360
agtctctcta taacatctga gtaagtggcg gctgcgacaa tgctactgga gttccagaat     420
cgtgttggtg acaagattgt tcaccagcat atggtgtggt gaaaactcac taatttggaa     480
ttagttcaga ttattaagcc tgaataggtg aaaatcctga atcaaggat ctttggaact     540 atttgaaatc agtatttat attttcctgt tgtattcatt aaagtgttgc aagtgttcta      600
tttgatggat taagtatatt taggatatac atgttcaatt tgtgattttg tatacttaat     660
tggaacaaga aagctaataa aggttttgat atggacatct attctttaa gtaaacttca     720 atgaaaatat atgagtagag catatagaga tgtaaataat ttgtggacac accacagact     780
gaaatagcaa atttaaaaga aattgttgga agaatcaagt gtttgtggaa tgagtcctcc     840
```

| | |
|---|---|
| tagtaaagtt cctgctcttg tgaataatta agcctcatgt ataattacta tagcaaaagg | 900 |
| aagcctaaga agtattagac tctacttgta tttaaattac attttacata atttatgtgt | 960 |
| atgaaaaatg ttttaaatgc ttatttcgt aagccatgag atagctcctt tatatttaa | 1020 |
| gaatttctga attaatttgc ttggatttta ttagtgcaaa tggcagagct agcaattcct | 1080 |
| ttttctgtgt tcccattcca tcctattcat ccctctttta ggaaactctg aactctggat | 1140 |
| tgtccttgtt tacatacctg cctcctgcat tggactatgt gtctctgagt gtagtatgac | 1200 |
| taattcattt gtttgtcaag gactctcaat gcatttgttg aacagcctaa ttagtaatgt | 1260 |
| ctgcaacaat gacattttac tgtatttaat aaagctctgg gaaagtagga tacacataag | 1320 |
| acaggtctag gtctaaattc tttacagaaa cttggatttt tagttcggtt tgaaatttga | 1380 |
| agatgtgagt atatttatct cagtttccca aaggacaagc taattggaat tatcatcctc | 1440 |
| tttcacttga ttggatcccc agaatgccat ttacgcatgc agcaggattt tataacagtt | 1500 |
| ttaaattctg tatatttgat gaagaggttt tatattttg gattcaagcc tcttttaaa | 1560 |
| cttctacaat atggtttaca ataattcctt atatcctgct tttgaaatac atattacaac | 1620 |
| tttttaagtt tggaaggcta tatttcaagg actgaagtta cagtatactc aagtgataca | 1680 |
| caagcctagc accccacttt ccacatagtg ttcgataaag attgataaac tcgaaatcac | 1740 |
| agaccttta attcttaaga caaatagcag cagaaagaaa catctttggc ttatttctgg | 1800 |
| taaggttttt atgctctgta aaacaaagaa ttgtattcat ccgcgcagca cagattctat | 1860 |
| taaaaataaa tgtgagagtc gttaatgtag tactgctcat ttaccatcaa aattcacttt | 1920 |
| tcaggaataa tcccatcagt ttaaattgga tattggaatg agcattgatt acatttaact | 1980 |
| tggtagccca aaatttcttc atggggtttt gaactcggcg ggatttcaaa ggttttaaaa | 2040 |
| atgagttttt gattttttt aaaaccctca aatttcatta cctttaaact aggtcgaaac | 2100 |
| ggggcgcaag agattggatt aacaccatag taatacttat tttgttctta accatttcag | 2160 |
| ggcttcttga aatagaggct gtatggtgta atggaaaaaa cagccttgga atctgggagc | 2220 |
| ctgattcctg gattcagtcc cagttttgcg tgaccttggg caagttactt tacttctctg | 2280 |
| aatttccgtt tcctcctctg caaaatgagg atcgcaatag ccaccttgca accttgactg | 2340 |
| gagcgagcct cgcacacccc gcgccggcct ggaggaagag cagccatgat tacgccgcct | 2400 |
| tcgctccgct acccgcttgc ggctggcgcc ctcctccagc aggtgtaggc gctgccgcgc | 2460 |
| tgccccacgc ctttccgccg ctcgcgggcc tgcgcctcgg cgtccccgag gaggccgctg | 2520 |
| cgggctgagg tagcgcaccg gcctctcggc gtccagtcc ggtccgggc ggagggaaag | 2580 |
| cgggcgaccc acctccgagg cagaagccga ggcccggccc cgccgagtgc ggaggagcgc | 2640 |
| aggcagcccc cgcccctcgg ccctcccccc ggccctcccg ccctccctc cgccccctcc | 2700 |
| gccctcgcgc gccgcccgcc cgggtcgccg cggggccgtg gtgtacgtgc agagcgcgca | 2760 |
| gagcgagtgg cgcccgtatg ccctgcgctc ctccacagcc tgggccgggc cgcccgggac | 2820 |
| gctgaggcgg cggcggcggc cgaggggggcc ggtcttgcgc tccccaggcc gcgcgcctg | 2880 |
| agcccaggtt gccattcgcc gcacaggccc tattctctca gccctcggcg gcgatgaggc | 2940 |
| gctgaggcgg ctgccggcgc tgcgccggag cttaggactc ggaagcggcc gggccgaggg | 3000 |
| cgtgggtgc cggcctccct gaggcgaggg tagcgggtgc atggcgcagt aacgccccct | 3060 |
| atctctctcc ccgctcccca gcctcgggcg aggccgtccg gccgctaccc ctcctgctcg | 3120 |
| gccgccgcag tcgccgtcgc cgccgccgcc gccgccatgg ccaatgacag cggcgggccc | 3180 |
| ggcgggccga gcccgagcga gcgagaccgg cagtactgcg agctgtgcgg gaagatggag | 3240 |

```
aacctgctgc gctgcagccg ctgccgcagc tccttctact gctgcaagga gcaccagcgt    3300
caggactgga agaagcacaa gctcgtgtgc cagggcagcg agggcgccct cggccacgga    3360
gtgggcccac accagcattc cggccccgcg ccgccggctg cagtgccgcc gcccagggcc    3420
ggggcccggg agcccaggaa ggcagcgcg cgccgggaca acgcctccgg ggacgcggcc     3480
aagggaaaag taaaggccaa gcccccggcc gacccagcgg cggccgcgtc gccgtgtcgt    3540
gcggccgccg gcgccagggg ctcggcgtg gctgccgaag ccgagcccgg caaggaggag     3600
ccgccggccc gctcatcgct gttccaggag aaggcgaacc tgtaccccc aagcaacacg     3660
cccggggatg cgctgagccc cggcggcggc ctgcggccca cgggcagac gaagcccctg     3720
ccggcgctga agctggcgct cgagtacatc gtgccgtgca tgaacaagca cggcatctgt    3780
gtggtggacg acttcctcgg caaggagacc ggacagcaga tcggcgacga ggtgcgcgcc    3840
ctgcacgaca ccgggaagtt cacggacggg cagctggtca gccagaagag tgactcgtcc    3900
aaggacatcc gaggcgataa gatcacctgg atcgagggca aggagcccgg ctgcgaaacc    3960
attgggctgc tcatgagcag catggacgac ctgatacgcc actgtaacgg gaagctgggc    4020
agctacaaaa tcaatggccg gacgaaagcc atggttgctt gttatccggg caatggaacg    4080
ggttatgtac gtcatgttga taatccaaat ggagatggaa gatgtgtgac atgtatatat    4140
tatcttaata aagactggga tgccaaggta agtggaggta acttcgaat ttttccagaa     4200
ggcaaagccc agtttgctga cattgaaccc aaatttgata gactgctgtt tttctggtct    4260
gaccgtcgca accctcatga agtacaacca gcatatgcta caaggtacgc aataactgtt    4320
tggtatttg atgcagatga gagagcacga gctaaagtaa aatatctaac aggtgaaaaa    4380
ggtgtgaggg ttgaactcaa taaaccttca gattcggtcg gtaaagacgt cttctagagc    4440
ctttgatcca gcaataccc acttcaccta caatattgtt aactatttgt taacttgtga     4500
atacgaataa atgggataaa gaaaaataga caaccagttc gcattttaat aaggaaacag    4560
aaacaacttt ttgtgttgca tcaaacagaa gattttgact gctgtgactt tgtactgcat    4620
gatcaacttc aaatctgtga ttgcttacag gaggaagata agctactaat tgaaaatggt    4680
ttttacatct ggatatgaaa taagtgccct gtgtagaatt ttttccattc ttatattttg    4740
ccagatctgt tatctagctg agttcatttc atctctccct tttttatatc aagtttgaat    4800
ttgggataat ttttctatat taggtacaat ttatctaaac tgaattgaga aaaaattaca    4860
gtattattcc tcaaaataac atcaatctat ttttgtaaac ctgttcatac tattaaattt    4920
tgccctaaaa gacctcttaa taatgattgt tgccagtgac tgatgattaa ttttattta     4980
cttaaaataa gaaaggagc actttaatta caactgaaaa atcagattgt tttgtagtcc     5040
ttccttacac taatttgaac tgttaaagat tgctgctttt tttttgacat tgtcaataac    5100
gaaacctaat tgtaaaacag tcaccattta ctaccaataa cttttagtta atgttttaca    5160
aggaaaaaga cacaagaaga gtttaaattt ttttgttttg ttttgttttt ttgagacagt    5220
cttgctctgt tacccaggct ggagggagt ggtgcattct tggctcactg caacctccgc     5280
ctcccaggtt caagcaatcc tcccacctca gcctcccaac tagctggac tgcaggcaca     5340
caccaccatg cctgactaat ttttgtatgt ttagtagaga cggggttttg ccatgttgcc    5400
taggctgggt tttaagttaa atttttaaa aaactaaagt gactggcact aagtgaactt     5460
gagattatcc tcagcttcaa gttcctaaga taagggcttt cttaagcttt caggtgtatg    5520
tatcctctag atgtagacaa taatgtccca tttctaagtc ttttcctttt gcttctcctt    5580
aaattgattg tacttccaaa tttgctgtta tgttttttc ctaatactgt gatctatctg     5640
```

-continued

```
atctgcagac aagaaccttg tctctgttga agagcatcaa ggggagatta tgtacacatt    5700
gaaactgaag tgtggtgtta ctgacggaat gtgcagtaac tcctcagata tctgttaagg    5760
catttcccag atgtgatgcc agccttctta cctgtactga agatgctta gcttagaaaa     5820 aaacaaaaca gatgcaaaat cagataattt tattttgttt catgggtttt cttatttact    5880
ttttaaacaa ggaaggaata ttagaaaatc acacaaggcc tcacatacat gttatttaaa    5940
gaatgaattg ggacggatgt cttagacttc actttcctag gcttttagc aaaacctaaa     6000 gggtggtatc catattttgc gtgaattatg ggtgtaagac cttgcccact taggttttct    6060
atctctgtcc ttgatcttct ttgccaaaat gtgagtatac agaaattttc tgtatatttc    6120
aacttaagac atttttagca tctgtatagt ttgtattcaa tttgagacct tttctatggg    6180
aagctcagta attttatta aaagattgcc attgctattc atgtaaaaca tggaaaaaaa     6240
ttgtgtagtg aagccaacag tggacttagg atgggattga atgttcagta tagtgatctc    6300
acttaggaga atttgcagga gaaagtgata gtttattgtt ttttcctcgc ccatattcag    6360
ttttgttcta cttcctcccc ttccttccag atgataacat cacatctcta cagtaagtgc    6420
ctctgccagc ccaacccagg agcgcaagtt gtctttgcca tctggtctat agtacagtgc    6480
gcggcgttag gccacaactc aaaagcatta tcttttttag ggttagtaga aattgtttta    6540
tgttgatggg aggtttgttt gattgtcaaa atgtacagcc acagcctttt aatttgggag    6600
cccctgttgt cattcaaatg tgtacctcta cagttgtaaa aagtattaga ttctactatc    6660
tgtgggttgt gcttgccaga caggtcttaa attgtatatt ttttggaaaa gtttatatac    6720
tctcttagga atcattgtga aaagatcaag aaatcaggat ggccatttat ttaatatcca    6780
ttcatttcat gttagtggga ctattaactt gtcaccaagc aggactctat ttcaaacaaa    6840
atttaaaact gttttgtggcc tatatgtgtt taatcctggt taaagataaa gcttcataat   6900
gctgttttta ttcaacacat taaccagctg taaaacacag acctttatca agagtaggca    6960 aagatttttca ggattcatat acagatagac tataaagtca tgtaatttga aaagcagtgt   7020
ttcattatga aagagctctc aagttgcttg taaagctaat ctaattaaaa agatgtataa    7080
atgttgttga aacattaaaa aa                                             7102
```

<210> SEQ ID NO 5
<211> LENGTH: 19
<212> TYPE: DNA
<213> ORGANISM: H. sapiens

<400> SEQUENCE: 5
cggaacaggc tatgtccgt                                                 19

<210> SEQ ID NO 6
<211> LENGTH: 19
<212> TYPE: DNA
<213> ORGANISM: H. sapiens

<400> SEQUENCE: 6
agactgggac gccaaggta                                                 19

<210> SEQ ID NO 7
<211> LENGTH: 19
<212> TYPE: DNA
<213> ORGANISM: H. sapiens

<400> SEQUENCE: 7
gtacagcgag catacgcca                                                 19

```
<210> SEQ ID NO 8
<211> LENGTH: 19
<212> TYPE: DNA
<213> ORGANISM: H. sapiens

<400> SEQUENCE: 8
caggtgagaa aggtgtgag                                                  19

<210> SEQ ID NO 9
<211> LENGTH: 43
<212> TYPE: DNA
<213> ORGANISM: H. sapiens

<400> SEQUENCE: 9
agatctcaag ttcctcacat gtgaggaact tgagatcttt ttt                       43

<210> SEQ ID NO 10
<211> LENGTH: 44
<212> TYPE: DNA
<213> ORGANISM: H. sapiens

<400> SEQUENCE: 10
gtacagccag catacgccat ggcgtatgct ggcttgtact tttt                      44
```

USE ON MINICIRCLE VECTORS FOR CARDIAC GENE THERAPY

Coronary artery disease (CAD) is the leading cause of morbidity and mortality in the Western world. Conventional treatment for CAD consists of medical therapy as the first-line strategy, followed by percutaneous coronary intervention (PCI) or coronary artery bypass graft (CABG). However, a significant number of patients will still have refractory angina despite these treatments. For such patients, the alternative approach of delivering potent angiogenic factors to stimulate new vessel growth has undergone intense investigation over the past decade. With the use of various gene transfer techniques, it is now possible to modify cardiac cells to overexpress beneficial proteins or inhibit pathologic proteins and achieve desired therapeutic effects. The field has expanded tremendously from preclinical studies in the early 1990s to large randomized clinical trials in the early 2000s. Although initial phase 1 trials in patients with myocardial ischemia provided encouraging results, recent phase 2 randomized trials (AGENT, VIVA, KAT) yielded only modest benefits. See, for example, Grines et al. (2002) Circulation 105(11):1291-1297; Hedman et al. (2003) Circulation 107(21):2677-2683; and Henry et al. (2003) Circulation 107(10):1359-1365. These inconsistencies have been attributed to the unclear role of single therapeutic genes such as vascular endothelial growth factor (VEGF) or fibroblast growth factor (FGF), as well as the inability to monitor gene transfer in vivo.

The introduction of an exogenous nucleic acid sequence (e.g., DNA) into a cell, a process known as "transformation," plays a major role in a variety of biotechnology and related applications, including research, synthetic and therapeutic applications. In many transformation applications, it is desirable to introduce the exogenous DNA in a manner such that it provides for long-term expression of the protein encoded by the exogenous DNA. Long-term expression of exogenous DNA is primarily achieved through incorporation of the exogenous DNA into a target cell's genome. One means of providing for genome integration is to employ a vector that is capable of homologous recombination. Techniques that rely on homologous recombination can be disadvantageous, however, in that the necessary homologies may not always exist; the recombination events may be slow; etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g., Maloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors include immunogenicity, viral based complications, as well as integration mediated mutation problems, and the like.

Therefore, there is continued interest in the development of additional methods of transforming cells with exogenous nucleic acids to provide for persistent, long-term expression of an encoded protein. Of particular interest is the development of a non-viral in vivo nucleic acid transfer protocol and vector that provides for persistent protein expression without concomitant genome integration, where the vector provides for persistent expression in a manner that is independent of the sequence and direction of the expression cassette present on the vector. Such methods may advantageously be applied to specific therapeutic methods.

Relevant Literature

Publications relevant to minicircle DNA vehicles Darquet et al. (1997) Gene Therapy 4(12):1341-1349; and Darquet et al. (1999) Gene Therapy 6(2):209-218. Also of interest are U.S. Pat. Nos. 5,985,847 and 5,922,687, and international application WO/11092.

Publications relevant to the relationship between HIF-1 activation and prolyl 4-hydroxylase-2 include Natarajan et al. (2006) Circulation Research 98(1):133-140; Chan et al. (2002) JBC 277(42):40112-40117; Hirota et al. (2005) Biochemical and Biophysical Research Communications. 338 (1):610-616; and Chan et al. (2005) MCB 25(15):6415-6426.

Publications relevant to the use of RNAi for ischemic heart disease include Huang et al. (2008) Circulation 118(14 Suppl):S226-233.

SUMMARY OF THE INVENTION

Compositions and methods are provided for the treatment of a cardiovascular condition, e.g. an ischemic cardiovascular condition, by providing a patient suffering therefrom with a minicircle DNA vector comprising polynucleotide sequences that potentiate HIF-1 activity, for a time and in an amount sufficient to stably and efficiently transduce cardiomyocytes involved in the cardiovascular condition. Treatment of coronary artery disease (CAD) in a human patient or an animal model for human disease is of interest. Treatment of peripheral vascular disease in a human patient or an animal model for human disease is also of interest.

The polynucleotide sequences are operably linked to a promoter that is active in muscle cells, e.g. cardiomyocytes or skeletal muscle, which includes inducible and constitutive promoters. Sequences that potentiate HIF-1 activity include, without limitation, RNAi, e.g. siRNA, shRNA, or anti-sense agents that decrease activity of prolyl hydroxylase proteins, e.g. PHD1, PHD2 and PHD3. Alternatively HIF-1, VEGF, etc. coding sequences may be provided, particularly where the HIF-1 is stabilized to normal degradation. After introduction of the vector and transduction of the muscle cells, the therapeutically-effective molecule is expressed in an amount effective to treat or ameliorate the cardiovascular condition.

Minicircle vectors provide significant advantages for myocardial or myogenic gene transfer. Minicircles show earlier onset and more robust transgene expression than conventional plasmids, and improve ventricular function and enhance neoangiogenesis for longer periods of time than conventional plasmids. Repeated injections of minicircles have comparable transgene activities over time, in contrast with viral vectors. Minicircle vectors have advantages over viral systems, including a better safety profile, and possibly easier good manufacturing practices (GMP).

In some embodiments, the minicircle vectors are optimized to remove expression-silencing bacterial sequences, where in many embodiments the subject vectors include a unidirectional site-specific recombination product sequence in addition to an expression cassette.

These and other objects, advantages, and features of the invention will become apparent to those persons skilled in the art upon reading the details of the invention as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 3:
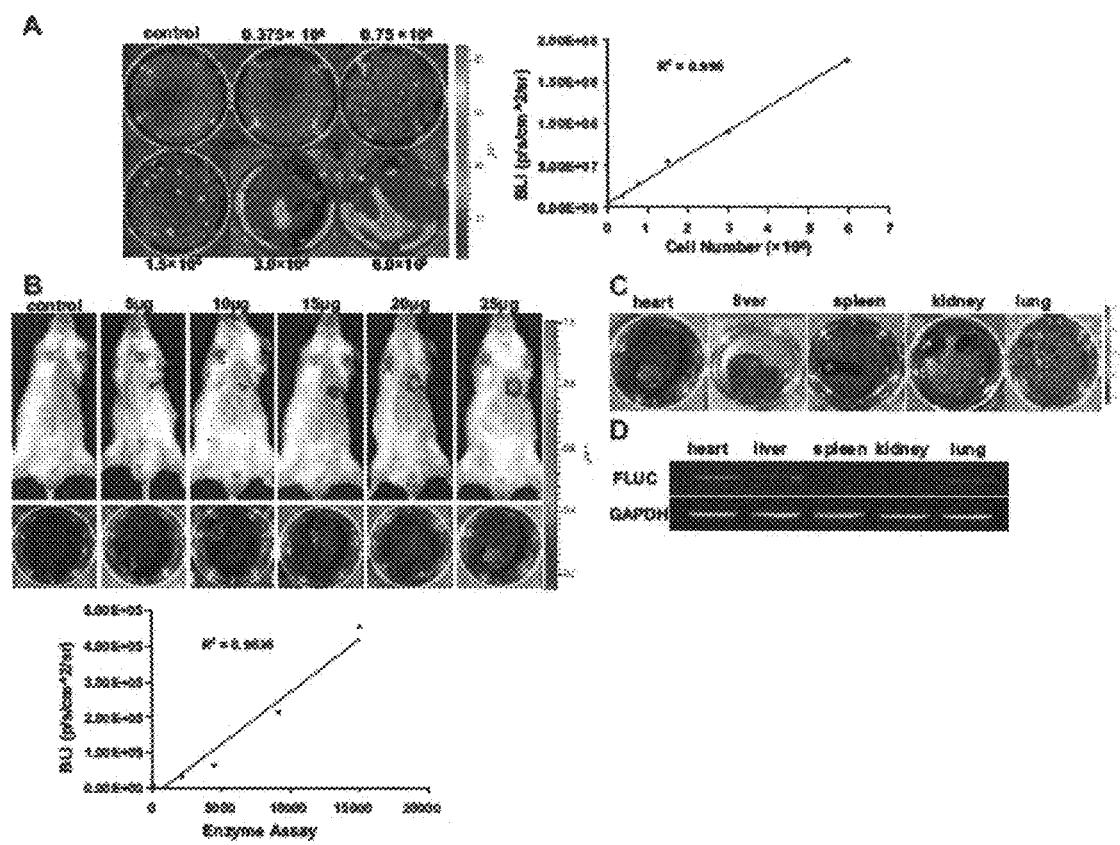
FIG. 3: Validation of imaging studies with traditional assays. (a) Mouse C2C12 myoblasts were transfected with the shPHD2 or shScramble plasmid. A robust correlation exists between transfected cell numbers and bioluminescence signals ($r^2=0.99$). (b) Mice were injected intramyocardially with different doses of shPHD plasmid (5-25 µg). Imaging analysis and enzyme assays of homogenized hearts show a robust correlation ($r^2=0.96$). (c) Representative image showing bioluminescence signals emitted from different organs of animals injected with shPHD2 plasmid immediately after harvest. (d) RT-PCR confirmed the Fluc transgene expression in the heart, liver, and lung but not spleen and kidney.

Representative H&E staining shows preservation of thicker heart wall mass after MC-HIF-1α treatment compared to PL-HIF-1α or PBS injections at week 8. (B) Immunofluorescence staining of CD31 endothelial marker (green) indicates increased small vessels in the myocardium following MC-HIF-1α and PL-HIF-1α therapy compared to PBS control. Cardiomyocyte staining is identified by trichrome (red; 100× magnification) Nuclear staining is identified by DAPI (blue; 100× magnification). (C-D) Representative Western blots and quantitative densitometric analysis of explanted hearts injected with MC-HIF-1α, PL-HIF-1α or PBS control at day 14. Significant upregulation of HIF-1α can be seen in the minicircle group. (E) Western blot shows higher activation of endogenous HIF-1α by LAD ligation compared to ischemia-reperfusion. Following delivery of MC-based gene therapy, HIF-1α levels are most robust at week 1 and decreases subsequently, coinciding with similar pattern of Fluc imaging signal decay seen in FIG. 3A. Sham: open thoracotomy only; I/R, ischemia/reperfusion; LAD: LAD ligation.

Figure 12:
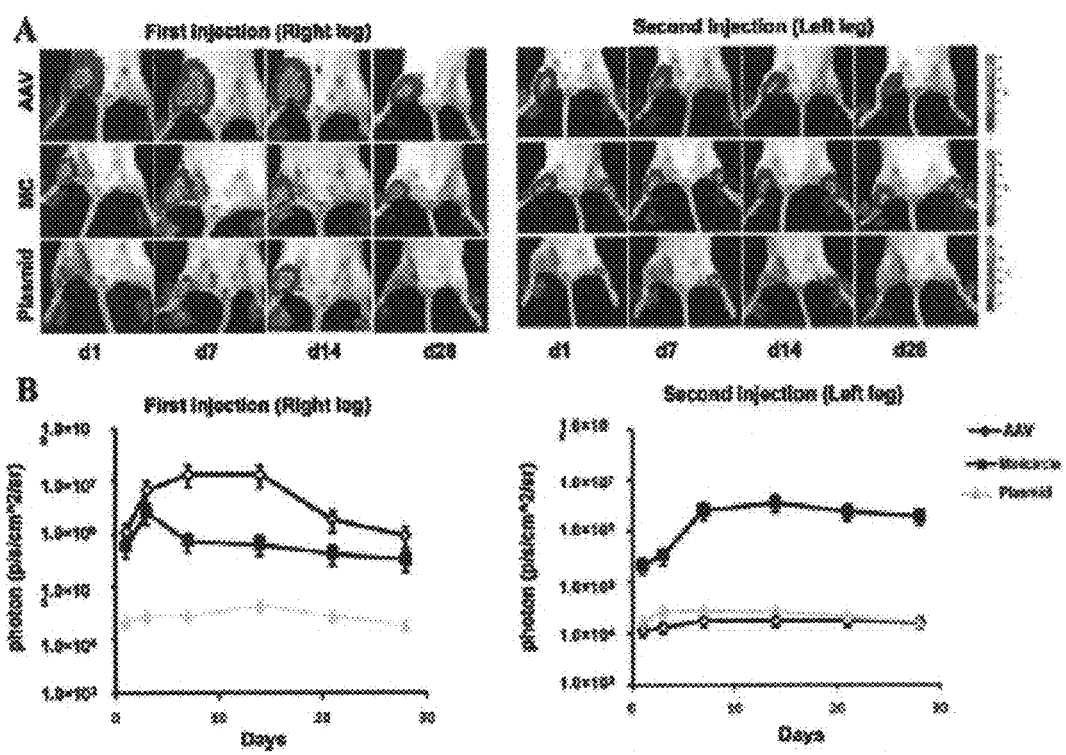

FIG. 12. Comparison of viral vs. non-viral mediated gene expression. (A) Representative BLI images of animals injected with AAV, minicircle, and regular plasmid in the right leg (first injection) followed by the left leg 28 days later (second injection). As expected, AAV expression is more robust compared to MC and plasmids initially. However, following repeat injection, AAV expression is not detected in the contralateral leg due to host mediated humoral immune respone. Color scale bar values are expressed as photons per second per square centimeter per steradian ($p/s/cm^2/sr$). (B) Graphical representation of longitudinal BLI after first and second injections in all three groups. Note that day 28 of second injection in left leg would represent day 56 of first injection in right leg in the same animal.

Figure 13:
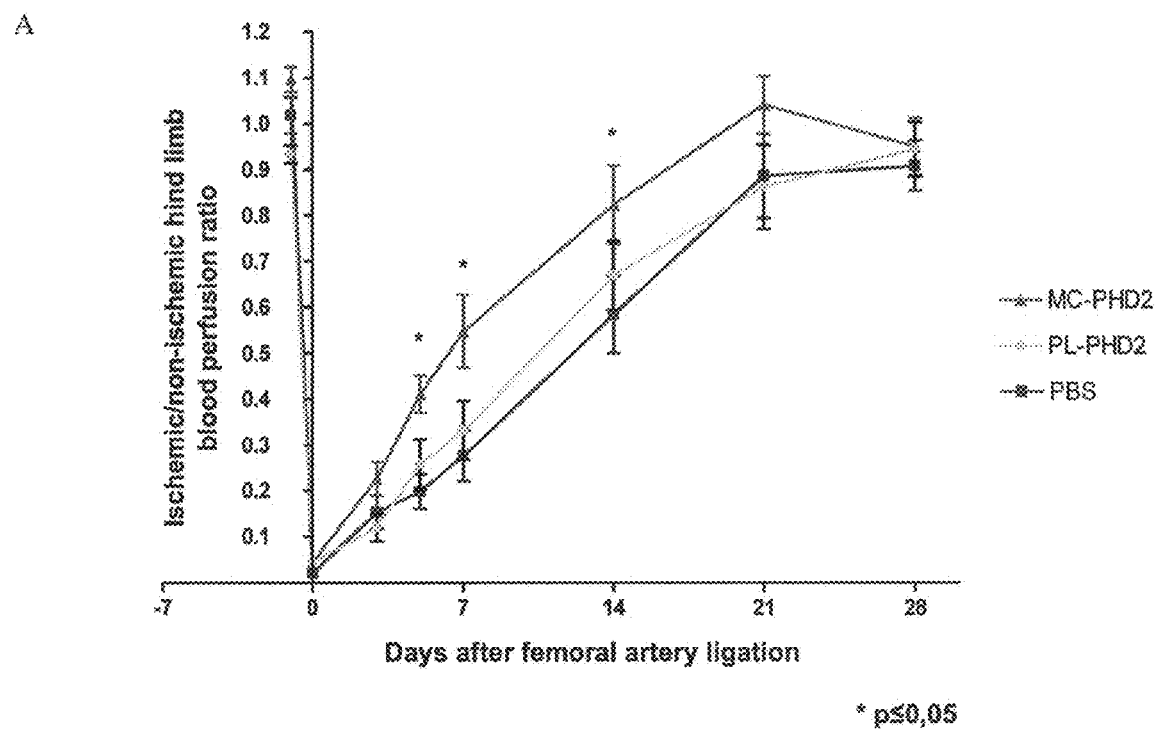
Figure 13:
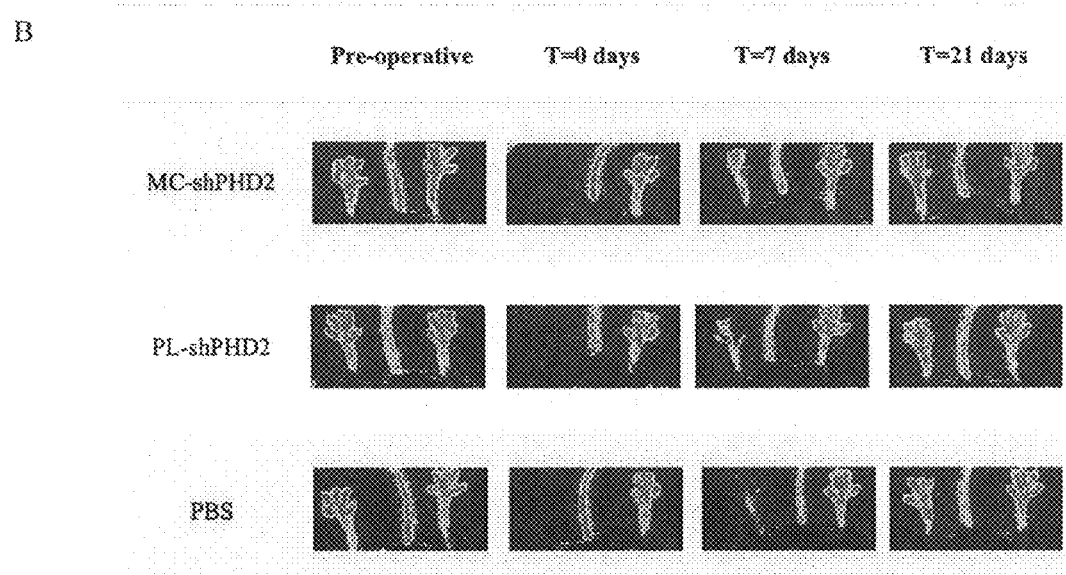

FIG. 13: LDPI measurement after induction of unilateral hind limb ischemia, by dual coagulation of the left femoral artery. A, Quantitative analysis of the LDPI measurements as a ratio of left to right limb. B, representative LDPI images.

Figure 14:
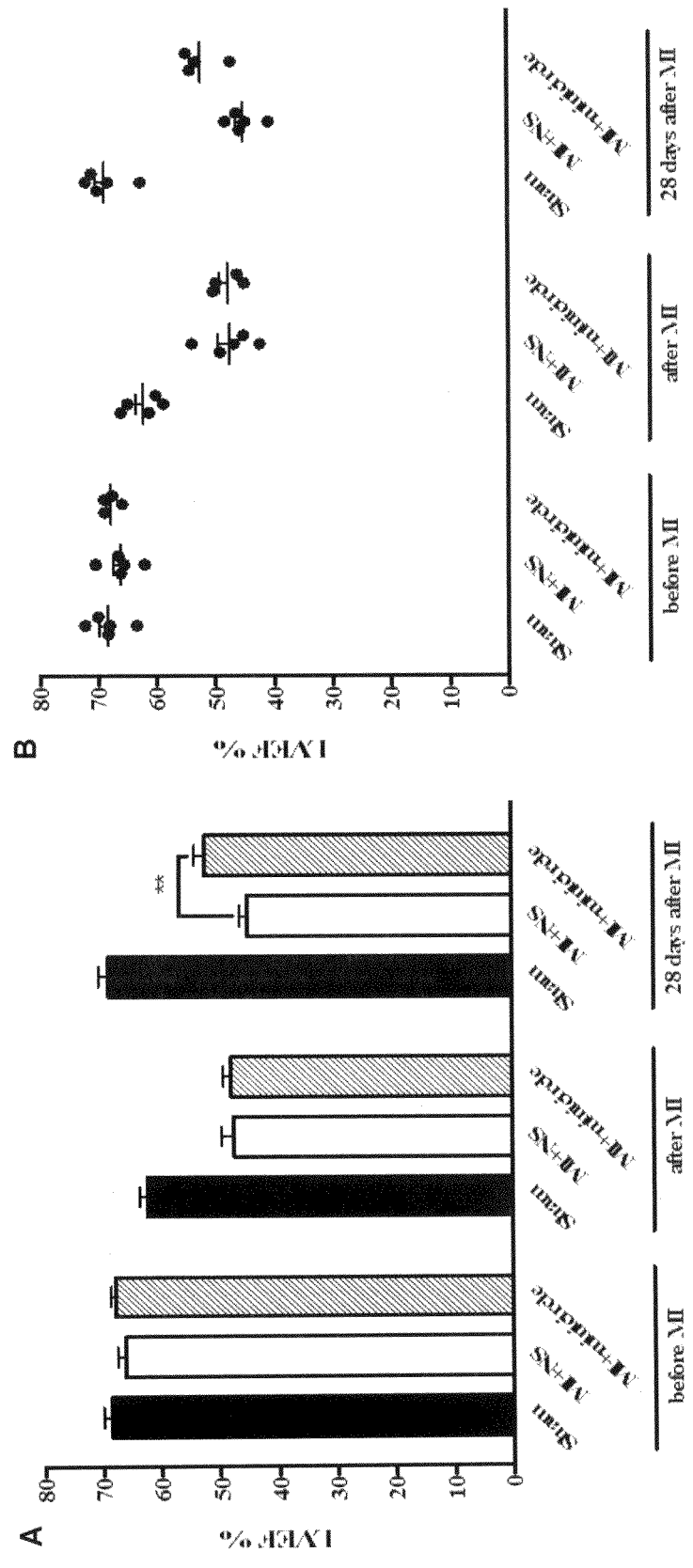

FIGS. 14A-B. Evaluation of left ventricular eject fraction by cardiac echocardiogarphy in sham, MI+normal saline, and MI+minicircle groups. After 4 weeks, the shPHD2 group showed significant improvement compared to the saline group.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The present invention provides methods of stimulating angiogenesis, typically in association with CAD or PVD, e.g. involving ischemia, by potentiating activity of HIF1. An example of a HIF1 potentiating agent is an inhibitor of PHD activity. PHD1, 2 and 3 are upstream negative regulatory genes in HIF-1 pathway. During hypoxia, when HIF-1α is stabilized, HIF-1 mediates transcriptional responses by binding to hypoxia-responsive elements (HRE) present on a series of target genes involved in metabolic adaptation, hematopoiesis, angiogenesis, and apoptosis. Under normal oxygenated conditions, HIF-1α is hydroxylated on two conserved proline residues, proline 402 or proline 564, by a family of prolyl-4-hydroxylases (PHDs).

PHD inhibition stabilizes HIF-1α stabilization, leading to induction of hypoxia inducible genes (e.g. HO-1 and GLUT-1), stimulation of angiogenesis, and protection against metabolic stress. HIF-1 plays a critical role in a variety of physiological processes, and upregulation of HIF-1α through PHD knock-down represents a new target in the field of cardiovascular gene therapy.

DEFINITIONS

Coronary Artery Disease. Coronary artery disease involves impairment of blood flow through the coronary arteries, most commonly by atheromas. Clinical presentations include silent ischemia, angina pectoris, acute coronary syndromes (unstable angina, MI), and sudden cardiac death. Diagnosis is by symptoms, ECG, stress testing, and sometimes coronary angiography. Treatment includes therapy to reduce ischemia and restore or improve coronary blood flow. In developed countries, coronary artery disease (CAD) is the leading cause of death in both sexes, accounting for about ⅓ of all deaths.

Usually, CAD is due to subintimal deposition of atheromas in large and medium-sized coronary arteries, also referred to as athersclerosis. Less often, CAD is due to coronary spasm. Rare causes include coronary artery embolism, dissection, aneurysm, and vasculitis.

Coronary atherosclerosis is often irregularly distributed in different vessels but typically occurs at points of turbulence (e.g., vessel bifurcations). As the atheromatous plaque grows, the arterial lumen progressively narrows, resulting in ischemia (often causing angina pectoris). The degree of stenosis required to produce ischemia varies with $O_2$ demand. Occasionally, an atheromatous plaque ruptures or splits. Rupture exposes collagen and other thrombogenic material, which activates platelets and the coagulation cascade, resulting in an acute thrombus, which interrupts coronary blood flow and causes some degree of myocardial ischemia. The consequences of acute ischemia, collectively referred to as acute coronary syndromes (ACS), depend on the location and degree of obstruction and range from unstable angina to transmural infarction.

Risk factors for CAD are the same as those for atherosclerosis: high blood levels of low density lipoprotein (LDL) cholesterol and lipoprotein a, low blood levels of high-density lipoprotein (HDL) cholesterol, diabetes mellitus (particularly type 2), smoking, obesity, and physical inactivity. Genetic factors play a role, and several systemic disorders, such as hypertension, hypothyroidism, hyperhomocysteinemia, etc. contribute to risk. A high level of apoprotein B (apo B) is an important risk factor; it may identify increased risk when total cholesterol or LDL level is normal.

High blood levels of C-reactive protein indicate plaque instability and inflammation and may be a stronger predictor of risk of ischemic events than high levels of LDL. High blood levels of triglycerides and insulin (reflecting insulin resistance) may also be risk factors. CAD risk may be increased by smoking; and dietary factors.

Treatment generally aims to reduce cardiac workload, improve coronary artery blood flow, and, over the long term, halt and reverse the atherosclerotic process. Coronary blood flow can be improved by percutaneous coronary intervention (PCI) or coronary artery bypass grafting (CABG). An acute coronary thrombosis may sometimes be dissolved by fibrinolytic drugs. However, CAD may progress despite bypass surgery. Postoperatively, the rate of proximal obstruction of bypassed vessels increases. Vein grafts become obstructed early if thrombi form and later (several years) if atherosclerosis causes slow degeneration of the intima and media.

Subjects for treatment with the methods of the invention include humans and other mammals, particularly mammals serving as laboratory models for human disease, e.g. murine, porcine, ovine, equine, rat, ungulates, dog, cat, monkey, and the like.

Peripheral arterial disease (PAD), also called peripheral vascular disease (PVD), is atherosclerosis of the extremities (virtually always lower) causing ischemia. Mild PAD may be asymptomatic or cause intermittent claudication; severe PAD may cause rest pain with skin atrophy, hair loss, cyanosis, ischemic ulcers, and gangrene. Diagnosis is by history, physical examination, and measurement of the ankle-brachial index. Conventional treatment of mild PAD includes risk factor modification, exercise, antiplatelet drugs, and cilostazol or possibly pentoxifylline as needed for symptoms. Severe PAD usually requires angioplasty or surgical bypass and may require amputation. Prognosis is generally good with treatment, although mortality rate is relatively high because coronary artery or cerebrovascular disease often coexists.

50 to 75% of patients with PAD also have clinically significant coronary artery disease (CAD) or cerebrovascular disease. However, CAD may be silent because PAD prevents patients from exerting themselves enough to trigger angina. Typically, PAD causes intermittent claudication, which is a painful, aching, cramping, uncomfortable, or tired feeling in the legs that occurs during walking and is relieved by rest. Claudication usually occurs in the calves but can occur in the feet, thighs, hips, buttocks, or, rarely, arms. Claudication is a manifestation of exercise-induced reversible ischemia, similar to angina pectoris. As PAD progresses, the distance that can be walked without symptoms may decrease, and patients with severe PAD may experience pain during rest, reflecting irreversible ischemia. Rest pain is usually worse distally, is aggravated by leg elevation (often causing pain at night), and lessens when the leg is below heart level. The pain may be burning, tightening, or aching, although this finding is nonspecific. About 20% of patients with PAD are asymptomatic, sometimes because they are not active enough to trigger leg ischemia. Some patients have atypical symptoms (e.g., nonspecific exercise intolerance, hip or other joint pain).

As ischemia worsens, ulcers may appear (typically on the toes or heel, occasionally on the leg or foot), especially after local trauma. The ulcers tend to be surrounded by black, necrotic tissue (dry gangrene). They are usually painful, but people with peripheral neuropathy due to diabetes or alcoholism may not feel them. Infection of ischemic ulcers (wet gangrene) occurs readily, producing rapidly progressive cellulitis.

RNA interference (RNAi). RNAi is an innate biological phenomenon that has evolved during mammalian evolution. Biologically, RNAi has an important role for the transient and long-term blocking protein expression. It is achieved by loading the RNA interference silencing complex (RISC) with a short single stranded antisense RNA that is complementary to a target mRNA.

By RNAi agent is meant an agent that modulates expression of a targeted sequence by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNAi agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments.

Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The shRNA containing the sense and antisense sequences from a target gene connected by a loop is transported from the nucleus into the cytoplasm where Dicer processes it into small/short interfering RNAs (siRNAs). At that point, it proceeds to knock down protein expression. The weight of the RNAi agents of the invention typically range from about 5,000 daltons to about 35,000 daltons, and in many embodiments are at least about 10,000 daltons and less than about 27,500 daltons, often less than about 25,000 daltons. In the methods of the invention, minicircle expression vectors are used to introduce the RNAi coding sequences into a cell.

While the Examples provided herein demonstrate shRNA suitable for inhibition of PHD2, one of skill in the art is readily able to utilize known methods and algorithms to determine other suitable sites for inhibition. For example, Lu et al. (2008) Nucleic Acids Res. 36(2):640-7 (herein incorporated by reference) discloses that accessibilities of siRNA and target mRNA for hybridization, as measured by folding free energy change, are shown to be significantly correlated with efficacy. A partition function calculation that considers all possible secondary structures can be used to predict target site accessibility. Other reviews and methods for siRNA selection include, inter alia, Peek and Behlke (2007) Curr Opin Mol Ther. 9(2):110-8; Pan and Clawson (2006) Curr Med Chem. 13(25):3083-103; and Tafer et al. (2008) Nat Biotechnol. 26(5):578-83 (each herein incorporated by reference).

Hypoxia-inducible factor-1 (HIF1) is a transcription factor found in mammalian cells in the presence of reduced oxygen tension, which plays an essential role in cellular and systemic homeostatic responses to hypoxia. HIF1 is a heterodimer composed of a 120-kD HIF1-alpha subunit complexed with a 91- to 94-kD HIF1-beta subunit. The 826-amino acid HIF1-alpha contains a bHLH (basic helix-loop-helix)-PAS domain at its N terminus. HIF1 mRNAs and proteins are induced in cells exposed to 1% oxygen and decay rapidly upon return of the cells to 20% oxygen. In cardiomyocytes, HIF1 is involved in myocardial ischemia.

HIF1 has a key role in cellular response to hypoxia, including the regulation of genes involved in energy metabolism, angiogenesis, and apoptosis. The alpha subunits of HIF are rapidly degraded by the proteasome under normal conditions but are stabilized by hypoxia. Cobaltous ions or iron chelators mimic hypoxia, indicating that the stimuli may interact through effects on a ferroprotein oxygen sensor. The von Hippel-Lindau tumor suppressor gene product VHL plays an important role in HIF1 regulation. In VHL-defective cells, HIF-alpha subunits were constitutively stabilized and HIF1 was activated. Reexpression of VHL restored oxygen-dependent instability. The interaction between HIF1 and VHL is iron dependent, and necessary for the oxygen-dependent degradation of HIF-alpha subunits.

HIF1 activity is controlled by the oxygen-regulated expression of the HIF1A subunit. Under nonhypoxic conditions, the HIF1A protein is subject to ubiquitination and proteasomal degradation. Sutter et al. (2000) Proc. Nat. Acad. Sci. 97: 4748-4753, herein specifically incorporated by reference, reported that missense mutations and/or deletions involving several different regions of the HIF1A gene result in constitutive expression and transcriptional activity in nonhypoxic cells.

In the presence of oxygen, HIF is targeted for destruction by an E3 ubiquitin ligase containing the VHL tumor suppressor protein. Human VHL protein binds to a short HIF-derived peptide when a conserved proline residue at the core of this peptide is hydroxylated. Because proline hydroxylation requires molecular oxygen and iron, this protein modification may play a key role in mammalian oxygen sensing. The interaction between VHL protein and HIF1-alpha subunit is therefore regulated through hydroxylation of proline by HIF-alpha prolyl-hydroxylase, also referred to PHD2.

As used herein the term "normoxia" or "normoxic" refers to a normal level of oxygen or oxygen tension in a cell or tissues. The term "hypoxia" or "hypoxic" refers to a lower level of oxygen or oxygen tension in a cell or tissue compared to what is normally found. Cells or tissues are hypoxic when the $O_2$ concentration is lower than the normal level of oxygen in these particular cells or tissues.

Hypoxia responsive elements (HRE). HREs are composite transcriptional regulatory elements, comprising a conserved binding site (HBS) with a core A/GCGTG sequence, and a highly variable flanking sequence. There are many sites with the core A/GCGTG sequence in the regulatory regions of mammalian genes. In addition to the obligatory core HBS sequence, compilation of data from more than 100 functionally verified HBSs revealed that certain nucleotide positions, other than the core A/GCGTG sequence, show a non-random character. Thus, A in the −1 position is 4.5 times over-represented, whereas T in the −3 position is 4.2 times under-represented. One of skill in the art can readily select from the many known mammalian, including human, HRE sequences. For example, specific sequences are described by Wenger et al. (2005) Sci STKE. (306):re12; and reviewed by Kaluz et al. (2008) Clin. Chim. Acta. 395(1-2):6-13, each herein specifically incorporated by reference.

Prolyl hydroxylase (PHD2). Posttranslational modification by prolyl hydroxylation is a key regulatory event that targets HIF subunits for proteasomal destruction via the von Hippel-Lindau ubiquitylation complex. In mammalian cells, the HIF-prolyl hydroxylases are represented by 3 proteins with a conserved 2-histidine-1-carboxylate iron coordination motif at the catalytic site. The genes encoding these proteins were cloned and termed PHD1, PHD2, and PHD3. Direct modulation of recombinant enzyme activity by graded hypoxia, iron chelation, and cobaltous ions mirrored the characteristics of I-HF induction in vivo, fulfilling requirements for these enzymes being oxygen sensors that regulate HIF. The genomic sequence of human PHD2 mRNA may be accessed at Genbank, accession number NM_022051, provided herein as SEQ ID NO:3 and SEQ ID NO:4. See Semenza (2001) Cell 107 (1)1-3; Taylor (2001) Gene 275 (1)125-132, each herein specifically incorporated by reference.

Minicircle Vector. As used herein a minicircle vector is a small, double stranded circular DNA molecule that provides for persistent, high level expression of a sequence of interest that is present on the vector, which sequence of interest may encode a polypeptide, an shRNA, an anti-sense RNA, an siRNA, and the like in a manner that is at least substantially expression cassette sequence and direction independent. The sequence of interest is operably linked to regulatory sequences present on the mini-circle vector, which regulatory sequences control its expression. Such mini-circle vectors are described, for example in published U.S. Patent Application US20040214329, herein specifically incorporated by reference.

The overall length of the subject minicircle vectors is sufficient to include the desired elements as described below, but not so long as to prevent or substantially inhibit to an unacceptable level the ability of the vector to enter the target cell upon contact with the cell, e.g., via system administration to the host comprising the cell. As such, the minicircle vector is generally at least about 0.3 kb long, often at least about 1.0 kb long, where the vector may be as long as 10 kb or longer, but in certain embodiments do not exceed this length.

Minicircle vectors differ from bacterial plasmid vectors in that they lack an origin of replication, and lack drug selection markers commonly found in bacterial plasmids, e.g. β-lactamase, tet, and the like. Consequently, minicircle becomes smaller in size, allowing more efficient delivery. More importantly, minicircle is devoid of the transgene expression silencing effect which is associated with the vector backbone nucleic acid sequences of parental plasmids from which the minicircle vectors are excised. The minicircle may be substantially free of vector sequences other than the recombinase hybrid product sequence, and the sequence of interest, i.e. a transcribed sequence and regulatory sequences required for expression.

A "vector" is capable of transferring nucleic acid sequences to target cells. For example, a vector may comprise a coding sequence capable of being expressed in a target cell. For the purposes of the present invention, "vector construct," "expression vector," and "gene transfer vector," generally refer to any nucleic acid construct capable of directing the expression of a gene of interest and which is useful in transferring the gene of interest into target cells. Thus, the term includes cloning and expression vehicles, as well as integrating vectors.

An "expression cassette" comprises any nucleic acid construct capable of directing the expression of any RNA transcript including gene/coding sequence of interest as well as non-translated RNAs, such as shRNAs, microRNAs, siRNAs, anti-sense RNAs, and the like. Such cassettes can be constructed into a "vector," "vector construct," "expression vector," or "gene transfer vector," in order to transfer the expression cassette into target cells. Thus, the term includes cloning and expression vehicles, as well as viral vectors.

By "polynucleotide of interest" or "sequence of interest" it is meant any nucleic acid fragment adapted for introduction into a target cell. Suitable examples of polynucleotides of interest include promoter elements, coding sequences, e.g. therapeutic genes, marker genes, etc., control regions, trait-producing fragments, nucleic acid elements to accomplish gene disruption, as well as nucleic acids that do not encode for a polypeptide, including a polynucleotide that encodes a non-translated RNA, such as a shRNA that may play a role in RNA interference (RNAi) based gene expression control.

The minicircle vectors may comprise a product hybrid sequence of a unidirectional site-specific recombinase, which product hybrid sequence is the result of a unidirectional site specific recombinase mediated recombination of two recombinase substrate sequences as they are known in the art, e.g., attB and attP substrate sequences, and may be either the attR or attL product hybrid sequence. Typically, the product hybrid sequence ranges in length from about 10 to about 500 bp. In certain embodiments, the product sequence is a product hybrid sequence of a unidirectional site specific recombinase that is an integrase, where integrases of interest include, but are not limited to: wild-type phage integrases or mutants thereof, where specific representative integrases of interest include, but are not limited to: the integrases of ΦC31, R4, TP901-1, ΦBT1, Bxb1, RV-1, AA118, U153, ΦFC1, and the like.

METHODS OF THE INVENTION

The methods of the invention provide an efficient and safe therapeutic regimen for potentiating the activity of HIF1 in a human or experimental mammal for the prophylactic or therapeutic treatment of ischemic cardiovascular disease, including coronary artery disease (CAD) and peripheral artery disease (PAD). The term "ischemic cardiovascular disease" refers to any abnormal condition of the arteries that interferes with the delivery of an adequate supply of blood to muscles or any portion thereof. Typically, CAD is caused by the accumulation of plaque on the arterial walls (i.e., atherosclerosis), particularly in the large and medium-sized arteries serving the heart, while PAD is caused by the accumulation of plaque on the peripheral arteries. Angina, which is a symptom of ischemia, can be caused by, for example, a coronary spasm, which is usually idiopathic, or the result of drug use, such as cocaine use. The lack of sufficient blood to muscle results in that tissue not having sufficient oxygen. In other words, some of the cardiac tissue is ischemic, which can lead to dysfunction or tissue cell death. The term "ischemic" refers to tissue that has become hypoxic (i.e., lacks sufficient oxygen), typically as a result of obstruction of the arterial blood supply or inadequate blood flow. The muscle tissue, therefore, will not function appropriately and, possibly, will not survive. The inventive method results in the stimulation of blood vessel growth, such that the ischemic muscle or ischemic portion of the muscle receives an increased amount of oxygen so that it is less ischemic, thereby resulting in the treatment. The muscle may be cardiac muscle, as with CAD, or may be skeletal muscle, as with PAD.

Cardiac muscle consists of three layers of muscle tissue: the epicardium (outer layer), the myocardium (middle layer), and the endocardium (inner layer). The cardiac muscle contains cells, such as cardiac myocytes, that can be transduced by a minicircle vector of the invention. The detection of an ischemic cardiac muscle can be performed using any suitable method known in the art. Diagnostic tests for cardiac ischemia are well known and include resting, exercise, or ambulatory electrocardiograms, scintigraphic studies (radioactive heart scans), echocardiography, coronary angiography, and positron emission tomography (PET).

The inventive method is directed to providing a treatment for CAD by contacting ischemic cardiac muscle with a minicircle vector comprising polynucleotide sequences that potentiate, or enhance, HIF1 activity. Sequences of interest include HIF1 coding sequences, e.g. stabilized HIF1 variants as described above; inhibitors of PHD activity, e.g. inhibitors of one or more of PHD1, PHD2 and/or PHD3. Inhibitors of interest include anti-sense molecules, siRNA, and shRNA that is targeted to the PHD sequence.

The method comprises introducing to ischemic cardiac muscle a dose of a pharmaceutical composition comprising (a) a pharmaceutically acceptable carrier and (b) a minicircle vector comprising a nucleic acid sequence encoding a HIF1 potentiating agent that is operably linked to a promoter. The vector may be introduced to the heart topically, e.g. by injection into cardiac muscle, or systemically, e.g. by i.v. injection.

The method comprises introducing to ischemic skeletal muscle associated with PAD a dose of a pharmaceutical composition comprising (a) a pharmaceutically acceptable carrier and (b) a minicircle vector comprising a nucleic acid sequence encoding a HIF1 potentiating agent that is operably linked to a promoter. The vector may be introduced to the muscle topically, e.g. by injection into muscle, or systemically, e.g. by i.v. injection.

Methods for the administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), by uptake of "naked DNA", and the like. Techniques well known in the art for the transformation of cells. The exact formulation, route of administration and dosage can be chosen empirically. (See e.g. Fingl et al., 1975, in "The Pharmacological Basis of Therapeutics", Ch. 1 pl).

The route of administration of the vector to the multicellular organism depends on several parameters, including: the nature of the vectors that carry the system components, the nature of the delivery vehicle, the nature of the multicellular organism, and the like, where a common feature of the mode of administration is that it provides for in vivo delivery of the vector components to the target cell(s) via a systemic route. Of particular interest as systemic routes are vascular routes, by which the vector is introduced into the vascular system of the host, e.g., intracoronary injection by cardiac catheters or intravenous injection.

Any suitable delivery vehicle may be employed, where the delivery vehicle is typically a pharmaceutical preparation that includes an effective amount of the vector present in a pharmaceutically acceptable carrier, diluent and/or adjuvant. In certain embodiments, the vector is administered in an aqueous delivery vehicle, e.g., a saline solution. As such, in many embodiments, the vector is administered intravascularly, e.g., intraarterially or intravenously, employing an aqueous based delivery vehicle, e.g., a saline solution.

In many embodiments, the vector is administered to the multicellular organism in an in vivo manner such that it is introduced into a target cell of the multicellular organism under conditions sufficient for expression of the nucleic acid present on the vector to occur. A feature of the subject methods is that they result in persistent expression of the nucleic acid present thereon, as opposed to transient expression.

In some embodiments of the invention, intramyocardial injection is preferred. The composition may be administered to any region of the cardiac muscle, including the cardiac tissue that forms one or more of the heart chambers (i.e., the left atrium, the right atrium, the left ventricle, and the right ventricle), for example to all or part of the outer wall and/or septum of the heart chamber. Alternatively, or in addition, the pharmaceutical composition is administered to all or part of the septum of the heart. The pharmaceutical composition can be administered to other regions of the cardiac muscle within the heart, including the papillary muscles of the left and right ventricles. The pharmaceutical composition may be administered to two or more regions of the cardiac muscle for effective delivery. For example, the pharmaceutical composition can be administered to the cardiac muscle forming a ventricle and an atrium, both atria, both ventricles, an atrium and the septum, and/or a ventricle and the septum (preferably, the left ventricle and the septum).

Any suitable means of administering the pharmaceutical composition to the cardiac muscle can be used within the context of the invention. Where the administration is localized it may be accomplished by directly injecting the pharmaceutical composition into the cardiac muscle. Any suitable injection device can be used within the context of the invention, e.g. a common medical syringe. To access cardiac muscle, the cardiac muscle can be exposed during a surgical procedure to allow for such injection. Minimally invasive delivery devices allow administration of the pharmaceutical composition to the cardiac muscle while avoiding more invasive medical procedures. Such devices are capable of accessing cardiac muscle not directly accessible through the skin, for example, via small incisions of less than 5 inches. Minimally invasive injection devices can comprise injector tips which are flexible and steerable to allow access via small incisions to the curved outer surface of the heart. An alternative means of non-invasive injection comprises the use of a needleless injection device. The pharmaceutical composition can be administered to a cardiac muscle using a catheter or a system involving a catheter. Endoscopy is similar to catheterization while permitting visualization of the cardiac muscle while administering the pharmaceutical composition. To allow for multiple injections with a specific geometry, a marking system can be employed so that the sites of previous injections are well delineated.

A single dose of the pharmaceutical composition may be administered via multiple injections to different points of the cardiac muscle. Any suitable number of injections can be utilized to administer the pharmaceutical composition to the cardiac muscle. The multiple injections typically will number from about 2 injections to about 50 applications or more (including all integers between 2 and 50), depending on the size of the cardiac muscle, the location and extent of ischemic tissue in the cardiac muscle, and the severity of the disease. Multiple injections provide an advantage over single injections in that they can be manipulated to conform to a specific geometry defined by the location of ischemic tissue in the cardiac muscle. In this way, too, the minicircle vector can be targeted to the cardiac muscle or a particular region thereof, such as the ischemic cardiac tissue of the cardiac muscle.

A feature of the minicircle vectors is that they provide for persistent expression of the encoded RNA present thereon, as opposed to transient or short-lived expression. By persistent expression is meant that the expression of the desired product is at a detectable level that persists for an extended period of time following administration of the vector. By extended period of time is meant at least 1 week, usually at least 2 months and more usually at least 6 months. By detectable level is meant that the expression of the encoded product is at a level such that one can detect the encoded product in target cell, or the mammal comprising the same, e.g., in the serum of the mammal, at a therapeutic concentration. Expression may persist for a period of time at a detectable level that is at least about 2 fold, usually at least about 5 fold and more usually at least about 10 fold longer following the subject methods as compared to a control. A product is considered to be at a detectable level if it can be detected using technology and protocols readily available and well known to those of skill in the art.

The expression module or expression cassette includes transcription regulatory elements that provide for expression of the desired product, and may be inducible, e.g. utilizing one, two three, four, five or more HRE in combination with a promoter; or may be constitutive. A variety of such combinations of transcriptional regulatory elements are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci. USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301-308)) and the like.

The particular dosage of vector that is administered depends on the nature of vector, the nature of the expression module and gene, the nature of the delivery vehicle and the like. Dosages can readily be determined empirically by those of skill in the art. For example, in mice where the vectors are directly administered in a saline solution vehicle, an effective dose of vector typically ranges from about 0.1 μg, 1 μg, 2.5 μg, 5 μg, 25 μg, 100 μg, 250 μg, 500 μg to 1000 μg/mouse. Where the host is a human, the dosage will be correspondingly increased to accommodate the larger size, e.g. ranging from about 1 μg, 2.5 μg, 5 μg, 25 μg; 100 μg, 250 μg, 500 μg, 1000 μg, 5 mg, 10 mg or more.

Any suitable pharmaceutically acceptable carrier can be used within the context of the invention, and such carriers are well known in the art. The choice of carrier will be determined, in part, by the particular site to which the pharmaceutical composition is to be administered and the particular method used to administer the pharmaceutical composition.

Suitable formulations include aqueous and non-aqueous solutions, isotonic sterile solutions, which can contain antioxidants, buffers, bacteriostats, and solutes that render the formulation isotonic with the blood or other bodily fluid of the human patient, and aqueous and non-aqueous sterile suspensions that can include suspending agents, solubilizers, thickening agents, stabilizers, and preservatives. Preferably, the pharmaceutically acceptable carrier is a liquid that contains a buffer and a salt. The formulations can be presented in unit-dose or multi-dose sealed containers, such as ampoules and vials, and can be stored in a freeze-dried (lyophilized) condition requiring only the addition of the sterile liquid carrier, for example, water, immediately prior to use. When the formulation is presented in a vial, the vial can be constructed of any material suitable for housing a pharmaceutical composition. The vial desirably is constructed of glass or plastic. The viral preferably is a glass vial. Glass vials are typically constructed of clear glass or tinted glass (e.g., green, blue, or amber), so as to protect a light-sensitive pharmaceutical composition contained therein from degradation. Preferably, the pharmaceutically acceptable carrier is a buffered saline solution.

The pharmaceutical composition can be maintained, formulated, packaged, and/or presented within a catheter, rather than, for example, a vial or ampule. Alternatively, the pharmaceutical composition can be maintained within a drug delivery cassette. Ideally, if the pharmaceutical composition is maintained within a drug delivery cassette, the drug delivery cassette can be placed into a catheter, which allows for release and dispersal of the pharmaceutical composition within the catheter.

The pharmaceutical composition preferably is formulated to protect the vector from damage prior to administration. The particular formulation desirably decreases the light sensitivity and/or temperature sensitivity of the adenoviral vector. Indeed, the pharmaceutical composition will be maintained for various periods of time and, therefore, should be formulated to ensure stability and maximal activity at the time of administration. The pharmaceutical composition can be maintained as a frozen formulation, that is, at a temperature below 0° C. The pharmaceutical composition desirably is maintained at a temperature above 0° C. and/or as a liquid, preferably at 4° C. or higher (e.g., 4-10° C.). It can be desirable to maintain the pharmaceutical composition at a temperature of 10° C. or higher, or even 30° C. or higher. The pharmaceutical composition can be maintained at the aforementioned temperature(s) for at least 1 day (e.g., 7 days (1 week) or more), though typically the time period will be longer, such as at least 3, 4, 5, or 6 weeks, or even longer, such as at least 10, 11, or 12 weeks, prior to administration to a patient. During that time period, the vector optimally loses no, or substantially no, activity, although some loss of activity is acceptable, especially with relatively higher storage temperatures and/or relatively longer storage times.

The effectiveness of the inventive method in treating coronary artery disease can be ascertained using any suitable parameter, such as those parameters currently used in the clinic to track occlusive arterial disease. Appropriate parameters include exercise electrocardiograms (ECGs), exercise tolerance test (EU), $^{99m}$Tc-sestamibi single photon emission computed tomography (SPECT), positron emission tomography (PET), magnetic resonance imaging (MRI), and quality of life questionnaires. Any of these parameters, alone or in any combination, can be used to evaluate the efficacy of the treatment of coronary artery disease in accordance with the invention. The parameters identified above, as well as other parameters suitable for evaluating the treatment efficacy of the invention, are described in, for example, Braunwald et al., Heart Disease: A Textbook of Cardiovascular Medicine, W.B. Saunders Company, Philadelphia, Pa. (6.sup.th ed. 2001), and Gibbons et al., J. Am. Coll. Cardiol., 30 (1), 260-311 (1997).

An electrocardiogram (ECG) detects and records the electrical activity of the heart during contraction. In patients with myocardial ischemia, the ST-segment tracing typically is more flat as the severity of the ischemic response worsens. With progressive exercise, the ST-segment deviates from baseline, and the patient may develop angina. Accordingly, ST-segment depression is of particular interest as a primary, and, optionally, a secondary parameter. ECGs typically will be used in the context of the invention to evaluate therapeutic response with respect to coronary artery disease.

Parameters measured by an exercise tolerance test (EU) include total exercise duration, time to onset of Level 2 angina or termination of EU in the absence of Level 2 angina, peak rate pressure product (heart rate.times.systolic blood pressure), and time to onset of at least 1 mm ST-segment depression or termination of EU in the absence of at least 1 mm ST-segment depression at 26 weeks after treatment by the inventive method. The angina scale for EU testing consists of 4 levels of angina. Level 1 angina is designated if the onset of angina is mild, but recognized as the usual "angina-of-effort" pain or discomfort with which the subject is familiar. In Level 2 angina, the subject experiences the same pain as in Level 1; however; the pain is moderately severe, definitely uncomfortable, but still tolerable. Level 3 angina is designated if the subject experiences severe anginal pain at a level that the subject will wish to stop exercising. In Level 4 angina, the subject experiences unbearable chest pain, which is the most severe pain the subject has felt.

$^{99m}$Tc-sestamibi SPECT is valuable in evaluation of a number of therapeutic assessments. For example, a $^{99m}$Tc-sestamibi SPECT can be used to determine a summed stress score, which is a semiquantitative measure of perfusion obtained by summing the severity scores of hypoperfusion of 20 segments obtained by post-stress images. The severity scoring is defined as: 0=normal, 1=mildly reduced or equivocal, 2=moderately reduced, 3=severely reduced, and 4=absent uptake.

A therapeutic effect resulting from the inventive method can be ascertained in any suitable manner and desirably is ascertained by comparing baseline values to follow-up values for any one or more of the above parameters. By "baseline values" is meant the values determined for each parameter performed in the baseline study recorded prior to treatment in accordance with the invention. By "follow-up values" is meant the values determined for the same parameter(s) as in the baseline study recorded at an appropriate time after treatment in accordance with the invention (e.g., 1 week, 6 weeks, 12 weeks, 26 weeks, 36 weeks, 48 weeks, or 52 weeks post-treatment). Typically, multiple follow-up studies are performed, and, thus, multiple follow-up values for the same parameters are ascertained at different time points post-treatment (e.g., two or more of 1 week, 6 weeks, 12 weeks, 26 weeks, 36 weeks, 48 weeks, and 52 weeks post-treatment). Suitable time points can be determined by the clinician.

Desirably, in accordance with the inventive method, the treatment of coronary artery disease in a human patient is evidenced by one or more of the following results: (a) at least a 5% increase, preferably at least a 10% increase (e.g., at least a 15% increase), in time to onset of at least 1 mm ST-segment depression on exercise electrocardiograms (ECG) or termination of exercise tolerance test (EU) in the absence of at least 1 mm ST-segment depression at 12 weeks post-treatment compared to time to onset of at least 1 mm additional ST-segment depression on ECG before treatment, or a similar or greater level of improvement using other clinical indicia. The treatment of coronary artery disease in a human patient alternatively, or in addition, is evidenced by an improvement in time to onset of angina during EU. In this respect, at least a one minute increase, preferably at least a 3 minute increase (e.g., at least a 4 minute increase or at least a 5 minute increase), in time to onset of angina during EU can evidence a therapeutic benefit of the treatment in accordance with the invention. The treatment of coronary artery disease in a human patient desirably is evidenced by one or more (in any combination) of the foregoing results, although alternative or additional results of the referenced tests and/or other tests can evidence treatment efficacy.

Also provided are kits for use in practicing the subject methods, where the kits may include one or more of the above components of the systems, e.g., minicircle vector, optionally including sequences encoding a HIF1 potentiating agent, and the like. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

The following examples are offered by way of illustration and not by way of limitation. It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

EXPERIMENTAL

Short Hairpin RNA Interference Therapy for Ischemic Heart Disease

The treatment of CAD may be improved by approaches based on the upstream transcriptional factor HIF-1α. HIF-1α is known to control the expression of over 60 genes that affect cell survival and metabolism in adverse conditions, including VEGF, FGF, insulin-like growth factor (IGF), erythropoietin, nitric oxide synthase, among others. Unfortunately, HIF-1α has a biological half-life of only ~5 minutes under normoxic condition. This is because during normoxic condition, HIF-1α is hydroxylated by oxygen-dependent PHD2, ubiquitylated, and subsequently degraded. Herein it is demonstrated that the inhibition of HIF-1α degradation via shRNA knockdown of PHD2 in the ischemic heart represents a novel angiogenic therapy approach. At the same time, we tracked the shRNA vector in vivo through novel molecular imaging technology.

During hypoxia, upregulation of hypoxia inducible factor-1 alpha (HIF-1α) transcriptional factor can activate several downstream angiogenic genes. However, HIF-1α is naturally degraded by prolyl hydroxylase-2 (PHD2) protein. Here we show that short hairpin RNA (shRNA) interference therapy targeting PHD2 can be used for treatment of myocardial ischemia and this process can be followed noninvasively by molecular imaging.

Materials and Methods

RNA interference of mouse PHD2 gene in culture cell: Mouse PHD2 gene was cloned from mouse ES cell after comparing human and rat homolog gene. We designed 4 sequences of RNA interference sites. The targeting sequences are shown in FIG. 1a. Sequence for the short hairpin scramble (shScramble) antisense is TGTGAGGAACTTGAGATCT (control). Construction of the H1 promoter driving sense and antisense, respectively, was performed as described. The fragment No. 2 knocking down site was inserted after H1 promoter in the vector pSuper as described in the Oligoengine™ manual.

Cell culture, shRNA transfection, and hypoxia exposure: Mouse C2C12 myoblasts were cultured in DMEM medium (high glucose) supplemented with 10% fetal bovine serum as described in the ATCC protocol. The sense and antisense fragments of mouse PHD2 driven by the H1 promoter were co-transfected into C2C12 with the plasmid pCMV-Fluc as control for equal transfection efficiency. Lipofectamine 2000 (Invitrogen) was used for the transfection according to manufacturer's protocol. Cells were cultured for 1 day after shRNA fragment transfection before being subjected to hypoxia. Hypoxia was achieved by placing cells in a hypoxia chamber filled with 5% $CO_2$, 1% $O_2$, and 94% $N_2$ at 37° C. Cells were then kept under hypoxic conditions for 48 hours. At the end of the hypoxic treatment, cells were harvested immediately to extract RNA and protein.

Animal surgery to induce myocardial infarction: Ligation of the mid left anterior descending (LAD) artery was performed in adult female FVB mice (Charles River Laboratories, Wilmington, Mass.) by a single experienced surgeon (GH). Myocardial infarction was confirmed by myocardial blanching and EKG changes. After waiting for 10 minutes, animals were then injected intramyocardially with 25 μg of shRNA plasmid at the peri-infarct zone (n=20) or 25 μg of shScramble plasmid (n=20) as control. In both groups, the volume of injection was 30 μl using a 31-gauge Hamilton syringe. Study protocols were approved by the Stanford Animal Research Committee.

Optical bioluminescence imaging of plasmid gene expression: Cardiac bioluminescence imaging was performed with the Xenogen In Vivo Imaging System (Alameda, Calif.). After intraperitoneal injection of the reporter probe D-luciferin (150 mg/kg body weight), animals were imaged for 1-10 minutes. The same mice were scanned repetitively for a 4-week period according to the specific study design. Bioluminescence signals were quantified in maximum photons per second per centimeter squared per steradian ($p/s/cm^2/sr$). Briefly, after anesthetic induction with 2% isoflurane, reporter probe D-luciferin (Promega) was injected into the peritoneal cavity. The animals were immediately placed in a light-tight chamber and baseline gray-scale body-surface images were taken. Afterwards, photons emitted from Fluc-luciferin photochemical reaction within the animal were acquired repetitively (1-10 minute acquisition time per image, 5-15 images per animal) until peak value was confirmed. We then averaged the 3 images with the highest p/sec/$cm^2$/sr values and used that to represent the Fluc transgene expression for that mouse on that particular day.

Validation of in vivo bioluminescence imaging with ex vivo enzyme assays: A subset of the animals (n=5) were injected with varying doses of the shPHD2 plasmid (5, 10, 15, 20, and 25 μg). Animals were sacrificed immediately following bioluminescence imaging. Different organs (heart, lungs, liver, kidney and spleen) were excised and placed in 6-well plastic dishes containing D-luciferin (100 μM). Ex vivo bioluminescence counts were determined. Afterwards, these organs were homogenized and luciferase enzyme assays performed using a luminometer (Turner Design-20/20).

Analysis of left ventricular function with echocardiogram: Echocardiography was performed before (day −7) and after (week 2, week 4, week 8) the LAD ligation. The Siemens-Acuson Sequioa C512 system equipped with a multi-frequency (8-14 MHZ) 15L8 transducer was used by an investigator (ZL) blinded to group designation. Left ventricular end diastolic diameter (EDD) and end-systolic diameter (ESD) were measured and used to calculate left ventricular fractional shortening by the formula: LVFS=[EDD-ESD]/EDD.

Histological examination: Explanted hearts from study and control groups were embedded into OCT compound (Miles Scientific, Elkhart, Ind.). Frozen sections (5 µm thick) were processed for immunostaining. To detect microvascular density (MVD) in the peri-infarct area, a rat anti-CD31 (BD Pharmingen) was used. The number of capillary vessels was counted by a blinded investigator in ten randomly selected areas using a light microscope (×200 magnification). Additional samples were used to examine the infarction size by Masson's trichrome staining.

Statistical Analysis: ANOVA and repeated measures ANOVA with post-hoc testing as well as the two-tailed Student's t-test were used. Differences were considered significant at P-values of <0.05. Unless specified, data are expressed as mean±standard deviation.

Results

Mouse PHD2 gene isolation and knocking down in culture cells. Based on the reported nucleotide sequence of PHD2 gene in rat and human, we isolated the PHD2 DNA clone from mouse ES cell (Sv129 line). We designed four siRNA sites (FIG. 1a) using a commercially available web-based software. To determine the site that possesses the optimal knocking-down efficiency, we cloned the sense and antisense downstream of the H1 promoter, respectively, by PCR method (Supplement. FIG. 1a). These 4 shRNA constructs were used to transfect C2C12 myoblasts in 6-well plates along with pCMV-luciferase plasmid used to confirm for equal transfection efficiency. After 48 hours of cell culture, mRNA levels of PHD2 within C2C12 cells were measured by RT-PCR. Using the densitometric analysis software, site 2 and site 3 inhibition could degrade 50-60% of the mouse PHD2 mRNA, which were significantly better than site 1 (15-25%) and site 4 (20-30%) (Supplement FIG. 1b).

Figure 1:
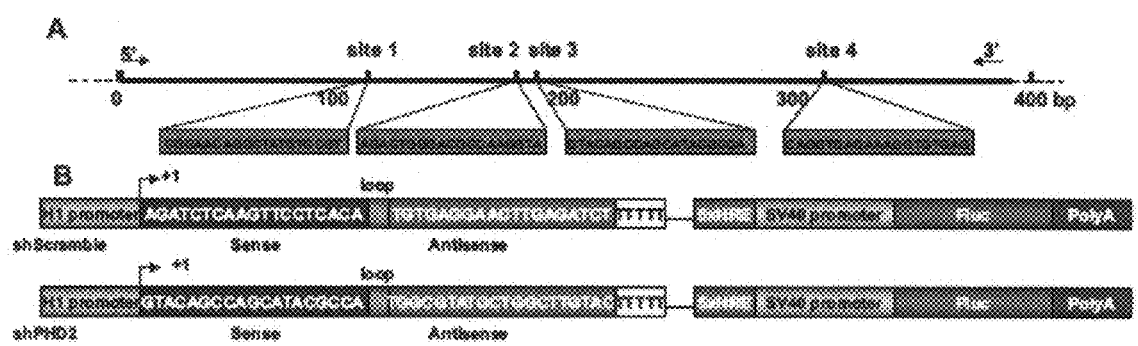
FIG. 1: Schema of the shPHD2 knockdown sites and reporter constructs. (a) Individual sequences of four siRNA target sites against the PHD2 gene (SEQ ID NOS:5-8). (b) Schema of classic hairpin carrying the site-2 sequence (shPHD2) and control hairpin carrying the scramble sequence (shScramble) (SEQ ID NO:9 and SEQ ID NO:10). The H1 promoter drives the expression of a hairpin structure in which the sense and antisense strands of the siRNA are connected by a 9-bp long loop sequence. In addition, a separate 5×HRE-SV40 promoter driving firefly luciferase (Fluc) is used to track shRNA activity in vitro and in vivo. 5× HRE, 5 repeat of hypoxia response elements; Sv40, simian virus 40.
Figure 2:
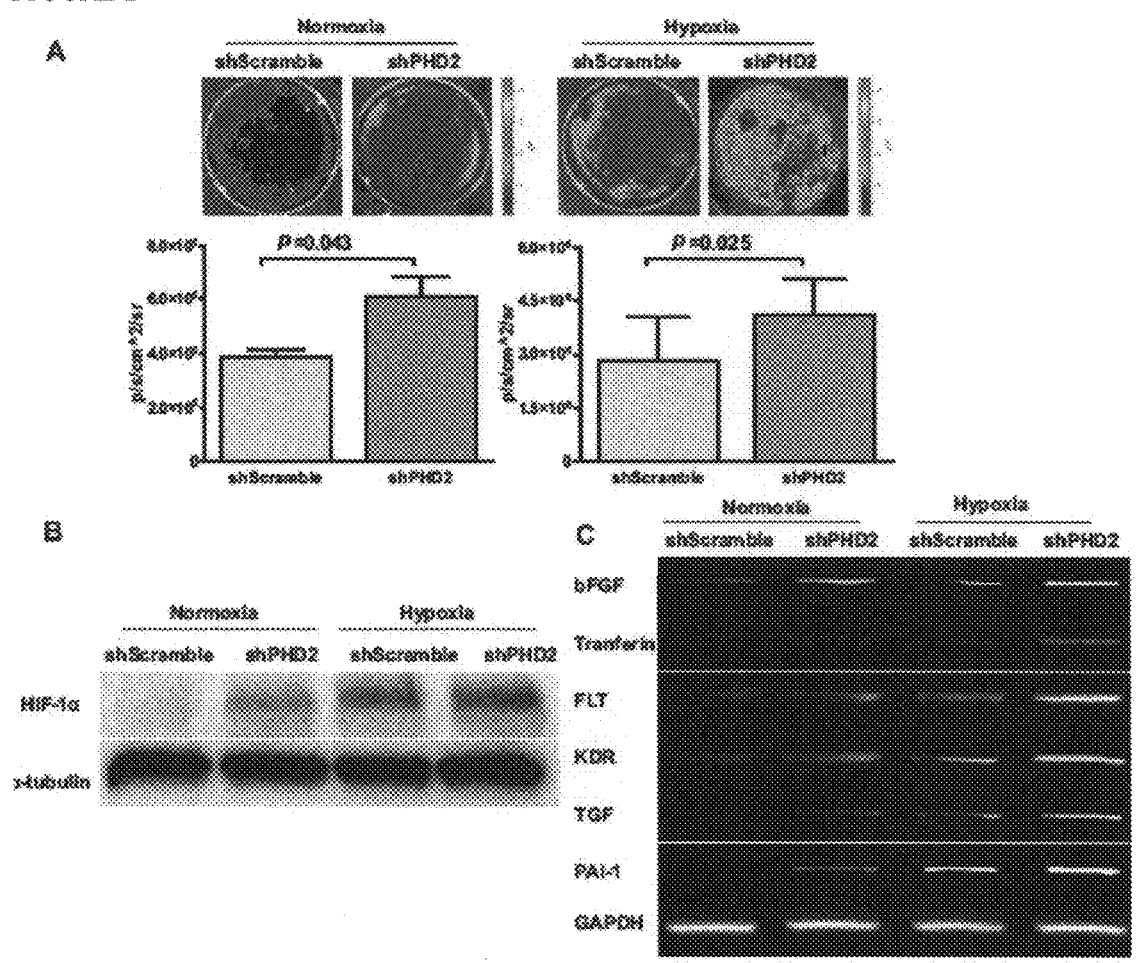
FIG. 2: In vitro characterization of mouse shPHD2 (a) In vitro imaging results indicate that Fluc signals increased significantly in response to shPHD2 therapy during both normoxia and hypoxia conditions via binding of HIF-1α protein on the 5×HRE binding site. (b) Western blot data show that levels of HIF-1α protein were more robust after shPHD2 plasmid transfection during normoxia and 6 hr hypoxia incubation. (c) RT-PCR analysis confirmed significant upregulation among 6 common genes involved in angiogenesis due to activation of the HIF-1α protein from knocking down PHD2 gene. GAPDH was used as the loading control.

In vitro characterization of shPHD2 under nomoxia and hypoxia conditions. In order to achieve in vivo inhibition via non-viral transfection, we constructed plasmid targeting PHD2 (shPHD2) by inserting the short hairpin structure downstream of the H1 promoter in a pSuper vector. A hypoxia sensing 5×HRE-SV40 promoter driving Fluc cassette was also inserted into the backbone of pSuper vector. The 5 copies of hypoxia response element (5×HRE) derived from the erythropoietin gene are activated through binding of the HIF-1 complex, and thus allow us to monitor the efficacy of the upstream shPHD2 knockdown compared to the upstream shScramble control (FIG. 1b). In the normoxic condition, cells transfected with shPHD2 had significantly higher Fluc bioluminescence signals compared to cells transfected with shScramble control, indicating increased binding of 5×HRE-SV40 promoter by HIF-1α following shPHD2 knockdown (FIG. 2a). As expected, a similar but more robust trend was observed when the cells were exposed to hypoxic condition. To confirm the imaging signals, nuclear extracts were isolated and Western blot analysis performed for detection of HIF-1α protein. As shown in FIG. 2b, robust HIF-1α stabilization was observed following exposure to hypoxia in shPHD2 transfected cells. The protein level was increased up to 50% after shPHD2 transfection. Upregulation of the HIF-1α pathway has been shown to activate several downstream genes responsible for stimulation of angiogenesis. To examine if upregulation of HIF-1α via shRNA knockdown of PHD2 can exert similar effects, total RNAs were extracted from C2C12 cells transfected with shPHD2. As shown in FIG. 2c, six common genes related to angiogenesis were increased by ~30% after shPHD2 treatment. Thus, both physiologic hypoxia and PHD2 knockdown can effectively stabilize HIF-1α and induce HIF-1α dependent gene activation in cell cultures.

Correlation of imaging signals with cell numbers, enzyme assays, and RT-PCR. In order to determine the validity of in vivo bioluminescence imaging with more conventional ex vivo assays, we first transfected different numbers of mouse C2C12 myoblasts ($0.375 \times 10^6$ to $6 \times 10^6$) with 4 µg of shRNA plasmid in six-well plates. As shown in FIG. 3a, the bioluminescence signals correlated robustly with in vitro Fluc enzyme activity ($r^2=0.99$) expressed as relative light unit per microgram protein (RLU/µg). Next, a subset of the animals (n=5) were injected with different doses of the shPHD2 plasmid (5-25 µg). At 1 week, bioluminescence signals were detectable in the heart, which also correlated robustly with the ex vivo Fluc enzyme activity ($r^2=0.96$). Finally, to determine the plasmid biodistribution following intramyocardial delivery, we explanted different organs from these animals. With this experimental setup, both bioluminescence imaging and RT-PCR analysis demonstrate that preence of Fluc transgene expression in the heart, liver, and lung but not spleen and kidney (FIG. 3c).

Tracking shPHD2 vector using bioluminescence imaging in living animals. Previously, Natarajan and colleagues have demonstrated the feasibility of small interfering RNA (siRNA) therapy for attenuating myocardial ischemia reperfusion injury. However, subsequent analysis showed that the actual knockdown target was to murine pro-collagen prolyl 4-hydroxylase-2 rather than HIF prolyl 4-hydroxylase-2. Here we confirmed our selection target with the GenBank database. Instead of using siRNA fragments which are only stable in vivo for 72 hours, we selected shRNA plasmid. We incorporated the 5×HRE-SV40 driving Fluc gene to track the shRNA expression activity. To evaluate the pharmacokinetics of shRNA in vivo, we injected the two shRNA plasmids into mice with myocardial infarction and followed their gene expression via Fluc bioluminescence imaging (FIG. 4a). As expected, mice injected with shPHD2 plasmid (bottom row) had significantly higher Fluc activity compared to mice injected with shScramble plasmid (top row). This can be attributed to the efficient knockdown of PHD2, resulting in more HIF-1α protein binding to the 5×HRE-Sv40 promoter site. For control animals injected with shScramble, endogenous activation of HIF-1α following myocardial infarction led to visible but lower Fluc signals. Quantitative analyses of Fluc activities for both groups are shown in FIG. 4b. Overall, infarcted animals had significantly higher activation of Fluc compared to non-infarcted animals during the first 2-4 week period.

Figure 5:
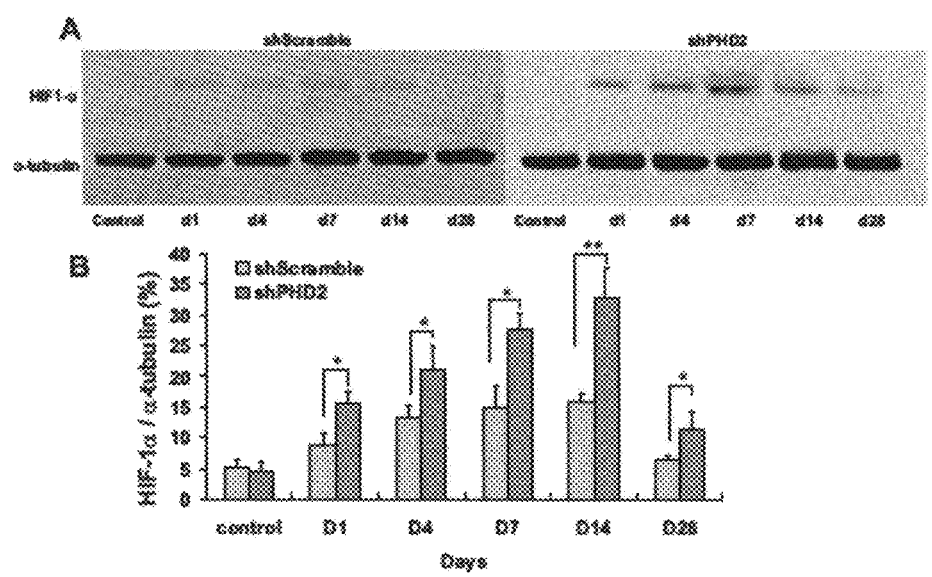
FIG. 5: Confirmation of HIF-1α activation in postmortem explanted hearts. (a) Western blots for day 1, day 4, day 7, day 14, and day 28 heart samples injected with shScramble (left) versus shPHD2 (right). Significant upregulation of HIF-1α can be seen in the shPHD2 therapy group within the first 2 weeks, coinciding with more robust Fluc bioluminescence imaging signal during the same time period. (b) Quantitative densitometric analysis of HIF-1α protein levels following shScramble and shPHD2 injections show a similar trend compared to the in vivo imaging results from FIG. 4.
Figure 6:
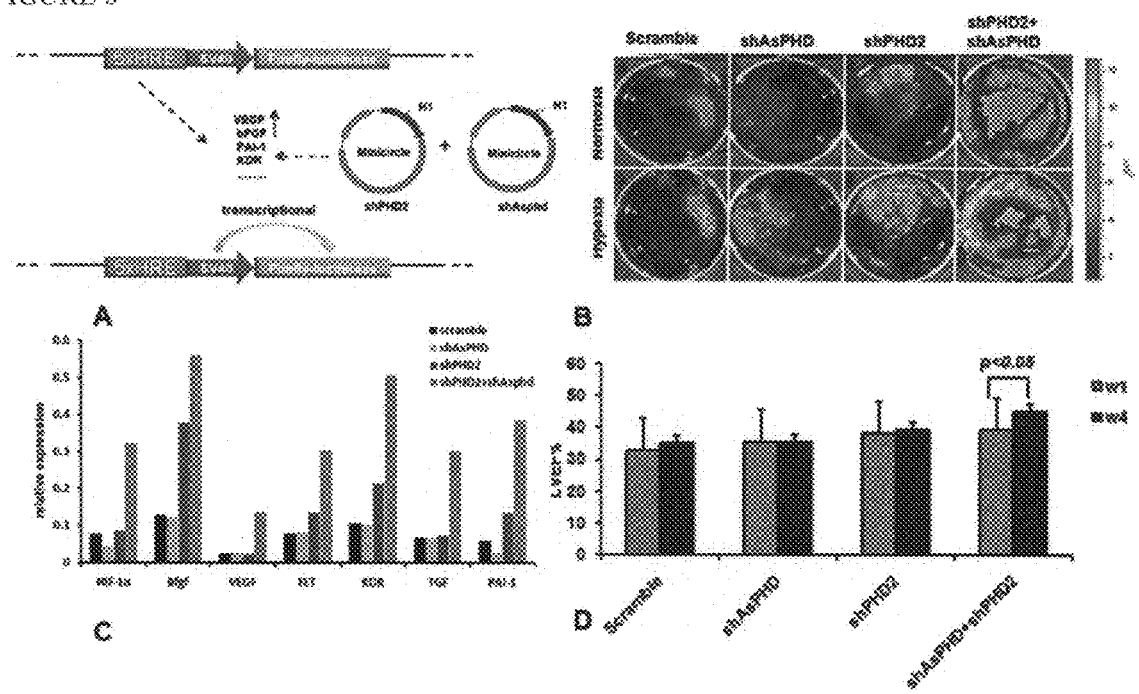
FIG. 6: (A) Schema of the 5×HRE-Fluc reporter construct used to monitor efficiency of shRNA knockdown. (B) C2C12 cells transfected with minicircles carrying both shPHD2+shAsPHD had the highest activation of Fluc expression. (C) Under normoxia and hypoxia conditions, double knockdown with shAsPHD+shPHD2 demonstrated higher levels of HIF-1a and more activation of downstream angiogenic gene expression. (D) Echocardiography shows that the double knockdown improved heart function more than single knockdown with either shAsPHD or shPHD2.

Injection of shPHD2 plasmid improved left ventricular ejection function. To examine whether shPHD2 therapy can also improve cardiac function following myocardial infarction, echocardiography was performed before (day −7) and after (week 2, week 4, week 8) the LAD ligation. At day −7, there was comparable LVFS between the shPHD2 group and shScramble control group. Following LAD ligation, the shPHD2 group had significantly higher LVFS (P=0.03) compared to the shScramble control group at week 2 and week 4 (Supplement FIG. 2a). However, this beneficial effect was no longer maintained by week 8 (shPHD2: 38.3±3.8% vs. shScramble: 36.8±2.1%; P=0.23). This is likely due to the limited short-term expression of plasmid-mediated shRNA expression within the first 4 weeks only, as shown by our imaging results (Supplement FIG. 2b). To confirm the functional imaging data, trichrome staining showed less infarction size for shPHD2 group compared to shScramble group at week 4. Immunohistochemistry of the peri-infarct region by CD31 staining also showed more neovascularization for the shPHD2 group compared to shScramble group (Supplement FIG. 3).

shPHD2 knockdown mediates HIF-1a upregulation in myocardial tissues. To further confirm the in vivo imaging data, we assayed for HIF-1α protein expression of explanted hearts at day 1, day 4, day 7, day 14, and day 28 following shPHD2 plasmid therapy (FIG. 5a). Quantitative analysis of the Western blot indicates that HIF-1α proteins were significantly higher in the shPHD2 treated hearts compared to shScramble treated hearts starting at day 1. Protein levels peaked at day 14 and returned back to baseline levels by week 4 (FIG. 5b).

We describe a novel shRNA therapy method which can also be tracked by noninvasive molecular imaging in a murine model of myocardial infarction. The major findings can be concluded as follows: (1) shRNA can be expressed consistently with two H1 promoters driving sense and anti-sense fragment, respectively. The sense and anti-sense fragment anneal automatically in cytoplasm to exert their knocking down effects; (2) down-regulation of the mouse PHD2 gene by plasmid-mediated short hairpin RNA interference (shPHD2) leads to activation of downstream angiogenic genes and proteins involved in the hypoxia response pathway as assessed by both in vitro and in vivo assays; (3) direct injection of shRNA targeting PHD2 can improve ventricular function and enhance neoangiogenesis in a mouse model of myocardial infarction during 4 week follow-up; (4) importantly, the pharmacokinetics of shRNA plasmid delivery can be monitored noninvasively in living subjects by a novel 5×HRE-SV40 binding site driving Fluc reporter gene; (5) intramyocardial delivery of plasmid can lead to extra-cardiac leakage and expression of Fluc transgene activity in other organs such as the liver and lung; (6) finally, a time-dependent decrease of Fluc signal activity was observed within a 4-week period due to plasmid degradation, which likely explains for the loss of cardiac functional recovery at 8 week follow-up.

In this study, we were able to track the HIF-1α upregulation through a novel noninvasive molecular imaging approach, avoiding the sampling biases and errors that may occur when different groups of animals are sacrificed at different time points. 5×HRE-SV40 promoter was inserted in front of the Fluc reporter gene. This hypoxia sensing construct can reflect the effects of shRNA plasmid expression through HIF-1α binding to the HRE element. For in vivo imaging signals, the plasmid expression reached peak activities between week 1 and week 2 (FIG. 4a). These results concur with the Western blot data of explanted hearts shown in FIG. 5a, which indicate that the HIF-1α activity (upregulated by shPHD2 knock-down) also increased during week 1 to week 2 and became degraded by week 4. Furthermore, the echocardiographic data showed improvement of heart function within the first month, confirming the Western blot and molecular imaging results. However, we also observed a time-dependent decrease of bioluminescence signal activity within this time period, indicating a loss of the shRNA plasmid. Thus, adoption of newer vectors that are less immunogenic such as minicircles or adeno-associated virus, may prolong gene expression and provide a more persistent functional recovery.

In summary, non-viral gene therapy through shRNA is a rapidly evolving area of investigation. With further validation, knocking down one or more regulatory factors involved in angiogenesis pathways as described here could provide a new avenue for treating myocardial ischemia. Furthermore, we believe molecular imaging can be a valuable tool in monitoring the localization; and activity of the shRNA vectors used for cardiovascular therapy. The in vivo information gathered is already generating useful insights and will enable better understanding of shRNA activity and mechanism in living subjects.

Example 2

Enhancing HIF-1α by Double shRNA Knockdown in Murine Myocardial Infarction

Ischemic heart disease (IHD) is the number one cause of morbidity and mortality in the US. In this study, we utilized a non-viral minicircle vector carrying two shRNA targeting sites. Under normoxic conditions, HIF-1α is hydroxylated at its Pro402 and Pro564 residues by HIF-1 prolyl hydroxylases (PHD2). In addition, the C-terminal transactivation domain of HIF-1α is hydroxylated at Asn803 by the factor inhibiting HIF-1 (AsPHD), which represses the transcriptional activity of HIF-1α. We hypothesis that double short hairpin RNA (shRNA) interference knockdown of PHD and AsPHD2 can be used for treatment of IHD by enhancing several proangiogenic genes downstream of HIF-1α.

Method: PHD2 and AsPHD was cloned from mouse embryonic stem cells. The best candidate shortairpin sequence for inhibiting PHD2 (shPHD2) and AsPHD (shAsPHD) was inserted into the minicircle vector with the H1 promoter. Another construct with SV40 promoter driving firefly luciferase was inserted coupled to hypoxia response elements (HRE) to allow molecular imaging of angiogenic response (FIG. 1). This construct was used to transfect mouse C2C12 myoblast cell line along with the shRNA constructs. Afterwards, shRNA constructs were injected intramyocardially following LAD ligation in adult FVB mice. Animals were randomized into shAsPHD group (n=10), shPHD2 group (n=10), shAsPHD+shPHD2 (n=10) versus control group with scramble sequence injection (n=10). Cardiac function was assessed by echocardiography at weeks 1 and 4.

Result: For in vitro cell culture, molecular imaging showed double knockdown expressed >50% higher angiogenesis level than shPHD2 group and >80% than scramble and shAsPHD group. Results are confirmed by quantitative PCR of 6 different angiogenesis gene. For in vivo study, echocardiography showed significant improvement of LVEF in the minicircle double knockdown group (45.2%±3.6%) compared to the single knockdown with shPHD2 (39.5%±4.1%) or shAsPHD (36.5%±2.8%) and scramble (35.5%±3.2%) groups at week 4 (P<0.05 for double knocking down).

This study demonstrates that double knockdown of PHD2 and AsPHD significantly increases HIF-1a, which lead to enhanced angiogenic gene response and improved cardiac contractility.

Example 3

Novel Minicircle Vector for Gene Therapy in Murine Myocardial Infarction

One of the most important objectives in gene therapy is the development of safe and efficient systems for gene transfer in eukaryotic cells. There are two strategies to provide target genes for gene transfer, viral and non-viral based systems. Although viral-based systems have shown high transfection efficiency in vivo, they suffer from serious disadvantages such as immunogenicity and inflammatory response. Nonviral gene delivery strategies are usually based on plasmid DNA carrying the gene of interest. Plasmid DNA is utilized in ~25% of all clinical gene therapy trials as of mid 2007.

Conventional plasmid vectors include a bacterial backbone and a transcription unit. However, these sequences may cause undesirable effects such as the production of antibodies against bacterial proteins expressed from cryptic upstream eukaryotic expression signals, changes in eukaryotic gene expression caused by the antibiotic resistance marker, and immune responses to CpG sequences.

Figure 7:
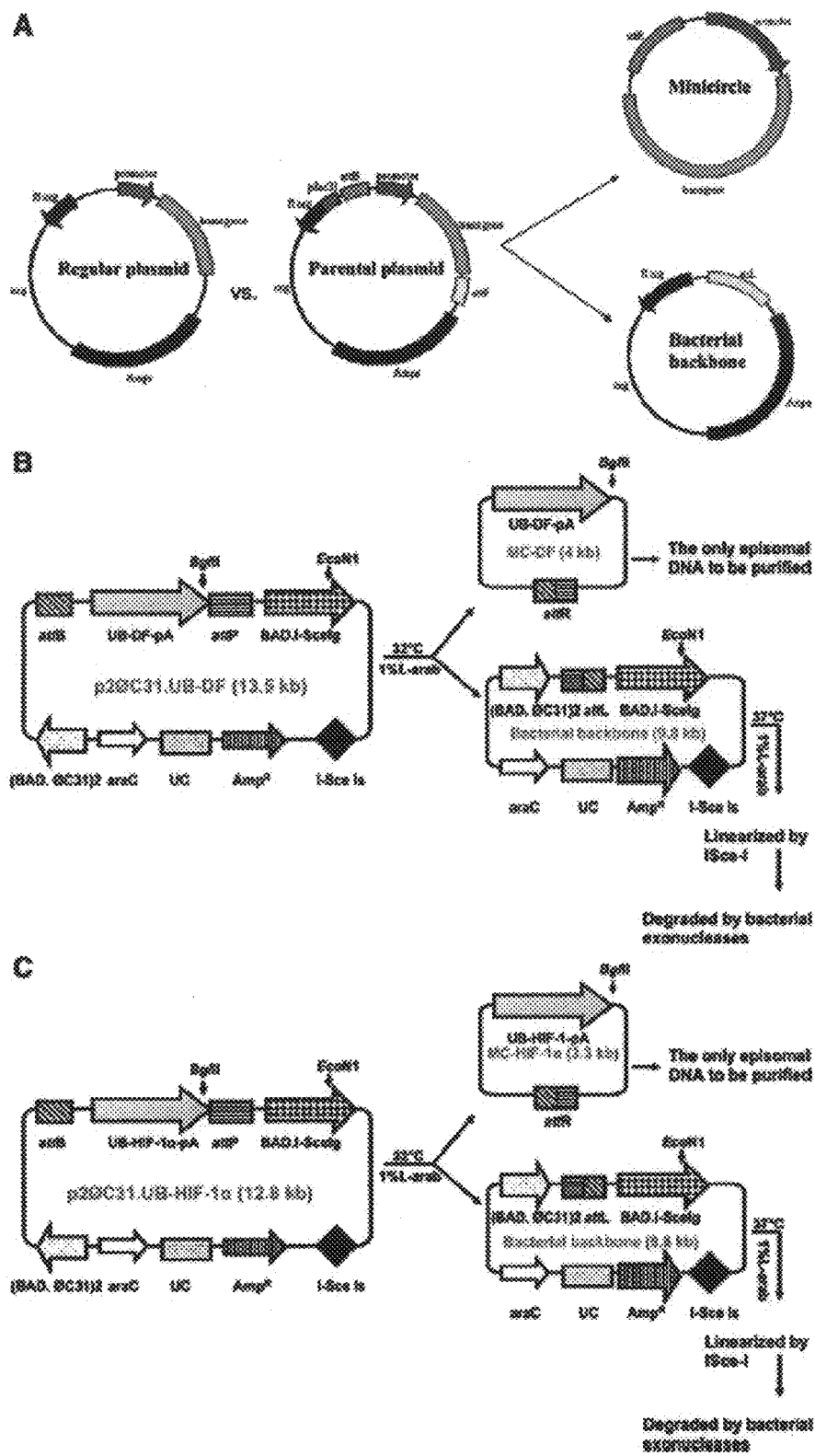
FIG. 7: Schema of the non-viral minicircle plasmid. (A) Minicircles are the product of site-specific recombination between the attB and attP sites driven by bacteriophage φC31 integrase. (B) Schema of the production process for minicircles carrying Fluc-eGFP double fusion reporter gene. By adding 1%-L-arabinose to the bacterial culture media, the aft sites of p2øC31.UB-DF were recombined to generate the minicircle DNA. The remaining circular bacterial backbone plasmids were linearized by I-SceI homing endonuclease and were removed by bacterial exonucleases at 37° C. (C) Schema of the production process for minicircles carrying HIF-1α therapeutic gene. In all three schemas, two circular DNAs are produced: one is the minicircle (MC), which contains the therapeutic gene cassette and the right hybrid sequence (attR), and the other is the bacterial backbone, containing the origin of replication and the antibiotic marker and the left hybrid sequence (attL), which is degraded after being restricted by ISce1. Eventually, the minicircle becomes the only episomal DNA which can be isolated using affinity column.

Conventional plasmids for gene therapy produce low-level and short-term gene expression. In this study, we develop a novel non-viral vector which robustly and persistently expresses the hypoxia inducible factor-1 alpha (HIF-1α) therapeutic gene in the heart, leading to functional benefits following myocardial infarction (MI). Compared to conventional plasmids, minicircles are supercoiled DNA molecules that are smaller and that lack a bacterial origin of replication and an antibiotic resistance gene. Minicircles are obtained in *E. coli* by att site-specific recombination mediated by the bacteriophage φ3I integrase (FIG. 7A). Minicircles may contain no more than an eukaryotic expression cassette and the attR fragment resulting from the attP/attB recombination event. Thus, they constitute a safe non-transmissible genetic material for nonviral gene therapy.

In this study, we have developed novel non-viral minicircles capable of transferring a reporter gene (Fluc-eGFP) and a therapeutic gene (HIF-1α) with higher efficiency than regular plasmids both in vitro and in vivo. Our results suggest that the use of minicircles may offer a promising avenue for safe and efficacious non-viral based cardiac gene therapy in the future.

Materials and Methods

Construction of minicircle plasmids. For the production of minicircle with ubiquitin promoter driving double fusion (MC-DF), firefly luciferase and enhanced green fluorescent protein (Fluc-eGFP) was amplified with FG-forward (5'-CCGAATTCATGAACTTTCTGCTGTCTTGGG) (SEQ ID NO:1) and FG-reverse (5'-AAAAGCGGCCGCTCATTCATTCATCAC) (SEQ ID NO:2) using pUbiquitin-Fluc-eGFP as a template (FIG. 1 B) (FG denotes Fluc/GFP). Amplification conditions are as follow: 2 min at 94° C. for initial denaturation, then 30 cycles of 30 sec at 94° C. for denaturation, 30 sec at 63.4° C. for annealing, and 1 min at 68° C. for extension, and then 10 min at 72° C. for the final extension. All PCRs were carried out in MyCycler™ (Bio-Rad, CA, USA). For the production of minicircle with ubiquitin promoter driving HLF-1a therapeutic gene (MC-HIF-1a), the DNA fragment which contains the ubiquitin promoter, the HIF-1αcDNA, and SV40 poly adenylation signal sequence was excised with EcoRI and XbaI from the pcDNA3.1-HIF-1α, and then bluntly ligated between the attB and attP sites of the p2ØC31 plasmid (FIG. 7C). Note we used a mutant version of the HLF-1α, which was created by site-specific mutation of P402 and P564 (P402A/P564G), rendering it less prone to hydroxylation and proteosomal degradation as previously described.

Preparation of minicircle DNA. *E. coli* Top10 (Invitrogen) was transformed by parental plasmids. A single colony of the transformants was grown in Terrif Broth (TB) at 37° C. overnight (OD600=4.5-5.0). The 1 L of bacterial culture in the steady state was spun down in a centrifuge (rotor JA-14, J2-MC centrifuge, Beckman, Fullerton, Calif., USA) at 1300 g for 15 min at 20° C. The pellet was re-suspended with 250-ml of fresh LB broth (pH 7.0) containing 1% L-(+)-arabinose. The resuspended bacteria were incubated at 32° C. with constant shaking at 225 rpm for 2 hr. Subsequently, 125-ml of fresh Low Salt LB broth (pH 8.0) containing 1% L-(+)-arabinose was added to the culture and the bacteria were cultivated for additional 2 hr at 37° C. for the activation of the restriction enzyme I-SceI, which cuts and linearizes the bacterial backbone plasmids and subject them for degradation (see FIG. 1). Super-coiled minicircle DNA was isolated from the culture, using plasmid purification kits from the Qiagen (Valencia, Calif.). The contaminated endotoxin in the DNA preparation was removed by the AffinityPak Detoxi-Gel (Pierce, Rockford, Ill.).

Cell culture and transfection. Mouse C2C12 myoblast cells were cultured in DMEM containing 10% fetal bovine serum (FBS). All cells were maintained in a 5% $CO_2$ incubator. For the transfection, cells were seeded at a density of $5 \times 10^5$ cells/well in the six-well flat-bottomed micro-assay plates (Falcon Co., Becton Dickenson, Franklin Lakes; NJ) 24 hr before the transfection. At 70-80% confluency, cells were transfected with 4 μg of plasmids carrying the double fusion reporter gene (PL-DF) or equimolar 2 μg of minicircles carrying the DF reporter gene (MC-DF) and incubated for an additional 48 hr. Lipofectamine 2000 (Invitrogen) was used for the transfection according to the manufacturer's protocol.

Noninvasive bioluminescence imaging (BLI) to assess duration of reporter gene expression. To compare the duration of gene expression in vivo, 25 μg of PL-DF and 12.5 μg of MC-DF were injected into normal mouse hearts following aseptic open thoracotomy (n=5 per group). BLI was performed with the Xenogen In Vivo Imaging System (Alameda, Calif.) on days 0, 1, 4, 7, 21, 42, 60, and 90 by an investigator blinded to study conditions (SH). After intraperitoneal injection of the reporter probe D-luciferin (150 mg/kg body weight), animals were imaged. The same mice were scanned repetitively according to the specific study design. BLI signals were quantified in maximum photons per second per centimeter squared per steradian ($p/s/cm^2/sr$) as described. Briefly, after anesthetic induction with 2% isoflurane, reporter probe D-luciferin (Promega) was injected into the peritoneal cavity. After waiting for 10 min to allow D-luciferin biodistribution, the animals were placed in a light-tight chamber and baseline gray-scale body-surface images were taken. Photons emitted from Fluc/D-luciferin photochemical reaction within the animal were acquired repetitively (1-10 min acquisition time per image, 5-15 images per animal) until peak value was confirmed. We then averaged the 3 images with the highest $p/sec/cm^2/sr$ values and used that to represent the Fluc transgene expression for that mouse on that particular day.

Animal surgery to induce myocardial infarction (MI). Ligation of the mid left anterior descending (LAD) artery was performed in adult female FVB mice (Charles River Laboratories, Wilmington, Mass.) by a single experienced microsurgeon (GH). MI was confirmed by myocardial blanching and EKG changes. After waiting for 10 min, animals were then injected intramyocardially with 12.5 pg of minicircles carrying HIF-1α (MC-HIF-1α), or equimolar 25 μg of regular plasmids carrying HIF-1α (PL-HIF-1α) as positive control, or PBS as negative control (n=10 per group). Injections were made near the peri-infarct region at 3 different sites with a total volume of 25 μl using a 31-gauge Hamilton syringe. Study protocols were approved by the Stanford Animal Research Committee.

Analysis of left ventricular function with echocardiogram. Echocardiography was performed before (day −7) and after (week 2, week 4, and week 8) the LAD ligation. The Siemens-Acuson Sequioa C512 system equipped with a multi-frequency (8-14 MHZ) 15L8 transducer was used by an investigator (ZL) blinded to group designation. Left ventricular (LV) end diastolic (EDV) and end-systole volume (ESV) were calculated by the bullet method as follows: $EDV = 0.85 \times CSA(d) \times L(d)$, $ESV = 0.85 \times CSA(s) \times L(s)$, where $CSA(d)$ and (s) are endocardial cross sectional areas in end-diastole and end-systole, respectively, obtained from short-axis view at the level of the papillary muscles and L(d) and L(s) are the LV length (apex to mid-mitral annulus plane) in end-diastole and end-systole, respectively, obtained from the parasternal long-axis view. The left ventricular ejection fraction was calculated as: LVEF %=(EDV−ESV)×100/EDV as described.

Western blot of mouse hearts to assess HIF-1α levels In order to determine the extent of HIF-1α activation following different experimental conditions, we randomized mice to sham surgery (open thoracotomy only), ischemia-reperfusion for 30 min, and LAD infarction (n=3 per group). Hearts from these animals were assayed for HIF-1α levels using Western blots on week 1, week 2 and week 3. After cutting the infarction part of the left ventricle under 10× microscope, we isolated tissue protein by Ripa buffer (Sigma). Protein concentration of lysis supernatant was determined by the DC protein assay (Bio-Rad protocol). Whole tissue extracts (25 μg) in equal volume of 2× loading buffer were run onto 10% Tris-glycine SDS-PAGE gels and transferred to Hybond ECL membrane (Amersham). Protein blots were analyzed with rat anti-mouse HIF-1α (1/500 dilution, Novus) followed by sheep anti-rat IgG whole antibody-HRP secondary (1/3000 dilution, Amersham) and developed using ECL assay (Amersham).

Histological examination. Explanted hearts from study and control groups were embedded into OCT compound (Miles Scientific, Elkhart, Ind.). Frozen sections (5 μm thick) were processed for immunostaining. To quantify the left ventricular infarct size, trichrome staining was done in PBS, plasmid, and minicircle-treated hearts (n=4 per group). For each heart, eight to ten sections from apex to base (1.2 mm apart) were analyzed. Images were taken for each section to calculate the fibrotic and non-fibrotic areas as well as ventricular and septal wall thickness. Scarring was determined as fibrotic area/(fibrotic+nonfibrotic area) as described. The NIH Image J software was used to quantify the infarct zones. To detect microvascular density (MVD) in the peri-infarct area a rat anti-CD31 (BD Pharmingen) was used. The number of capillary vessels was counted by a blinded investigator (FJ) in ten randomly selected areas using the picture under a fluorescent microscope ($\Delta$100 magnification). A typical green color vessel was selected as sample after opening one picture randomly by Image J software. The process was repeated 10 times in different per-infarct areas to calculate vessels numbers at 1 mm$^2$ scale. Additional samples were used to examine the infarction size by H&E staining.

Comparison of viral vs. non-viral vectors. In order to determine the duration of gene expression and the effects of immunologic response on viral vs. non-viral vectors, adult immunocompetent female FVB mice were injected with recombinant adeno-associated virus serotype 9 carrying CMV promoter driving firefly luciferase (AAV-Fluc at $1\times10^9$ pfu; gift from Roger Hajjar, Mount Sinai School of Medicine), 12.5 μg of MC-DF, or 25 μg of PL-Fluc in the right leg. Animals were imaged on days 1, 3, 7, 14, 21, and 28 using the Xenogen IVIS system. Afterwards, the same animals were injected with equal dosage of the same vectors into the left legs and imaging was performed at the same time points.

Statistical analysis. ANOVA and repeated measures ANOVA with post-hoc testing as well as the two-tailed Student's t-test were used. Differences were considered significant at P-values of $\leq 0.05$.

Results

Intramolecular recombination splits parental plasmid into minicircle and bacterial backbone. Minicircles are the product of site-specific intramolecular recombination between the attB and attP sites driven by bacteriophage φC31 integrase. After isolation from the bacterial backbone (FIG. 1A), the minicircles now lack both an origin of replication (cannot self-replicate) and an antibiotic selection marker (cannot confer resistance to other microorganisms), and carry only short bacterial sequences (greatly limiting immune responses against CpG sequences in the bacterial backbone). In this study, we first constructed MC-DF that allowed us to determine the transfection efficiency (in C2C12 cells) and duration of transgene expression (in living animals). The Fluc-eGFP cDNA was successfully cloned by PCR and ligated into the parental plasmid p2φc31.UB-DF (FIG. 7B). We next constructed MC-HIF-1α that allowed us to assess the therapeutic efficacy of MC vs. PL-based gene therapy approaches (FIG. 7C). The HIF-1α gene was successfully ligated into the parental plasmid p2φc31.UB-HIF-1α. We used the ubiquitin promoter (UB) for both parental plasmids because it has been shown to drive high levels of transgene expression with minimal gene silencing. By addition of arabinose at 32° C., the phage φC31 integrase performs a site-specific intramolecular recombination of sequences between attB and attP recognition sites, splitting p2φC31 parental plasmid into two supercoiled circular DNAs: the minicircle with its transgene of interest and another DNA circle comprising the remaining DNA with a "junk" bacterial backbone. To physically separate the two end products, we then adjust the pH and temperature to pH 8.0 and 37° C., respectively. The bacterial backbone plasmid is linearized by the induced I-SceI and degraded by bacterial exonucleases (FIG. 7B-7C). As a consequence, only the minicircle containing the transgene of interest in our study (DF and HIF-1α) remained intact as an episome formation in the bacterial cytosol, which can then be isolated for subsequent usage.

Figure 8:
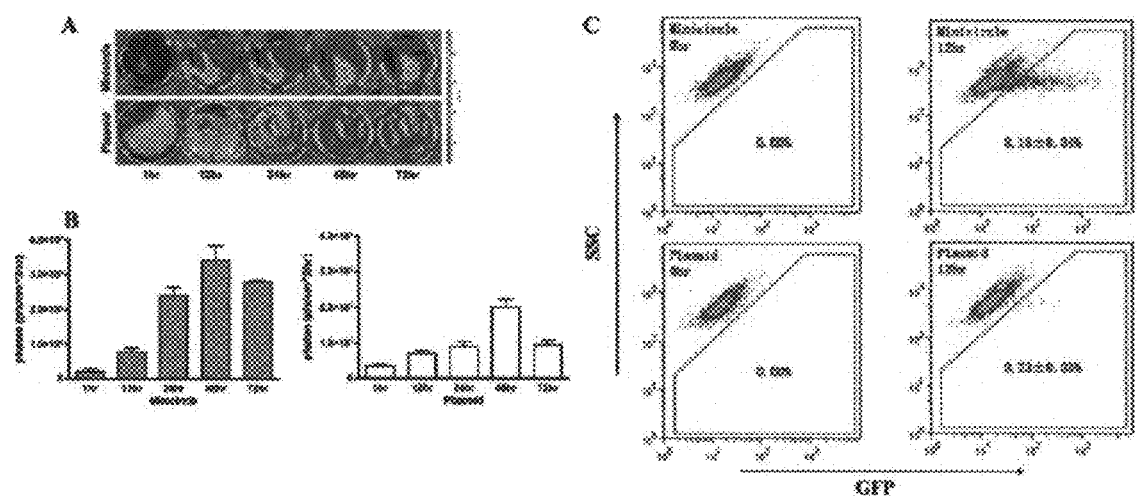
FIG. 8: Comparison of minicircles vs. regular plasmids in vitro. (A) The DF consists of Fluc and eGFP linked by a 5-amino acid linker (GSHGD). In vitro BLI shows that Fluc signals are significantly higher in C2C12 cells transfected with minicircles compared to plasmids at all time points. (B) Quantitation of Fluc indicates that minicircles are 5.5±1.7 (at 12 hr) and 8.1±2.8-fold (at 48 hr) higher than regular plasmid. Note the difference in Y-axis bars between the two plots. (C) eGFP expression through FACS at 12 hr coincides with the bioluminescence imaging results.

Evaluation of novel minicircles vs. regular plasmids in cell line. To assess the transfection efficiency, equimolar amounts of MC-DF and PL-DF were used to transfect mouse C2C12 cells. Fluc was evaluated by BLI (FIG. 8A) and eGFP evaluated by flow cytometry (FIG. 8B). MC-DF showed 5.5±1.7-fold (at 12 hr) and 8.1±2.8-fold (at 48 hr) higher Fluc expression compared to PL-DF. Since the DF is fusion construct whereby the two reporter genes are linked by a 5-amino acid linker (GSHGD), MC-DF also showed earlier onset of eGFP activity by 12 hrs (8.16±0.04 vs. 0.23±0.03%, P<0.01) as expected. Overall, these data demonstrate minicircles can mediate faster and higher transgene expression in vitro than regular plasmids.

Figure 9:
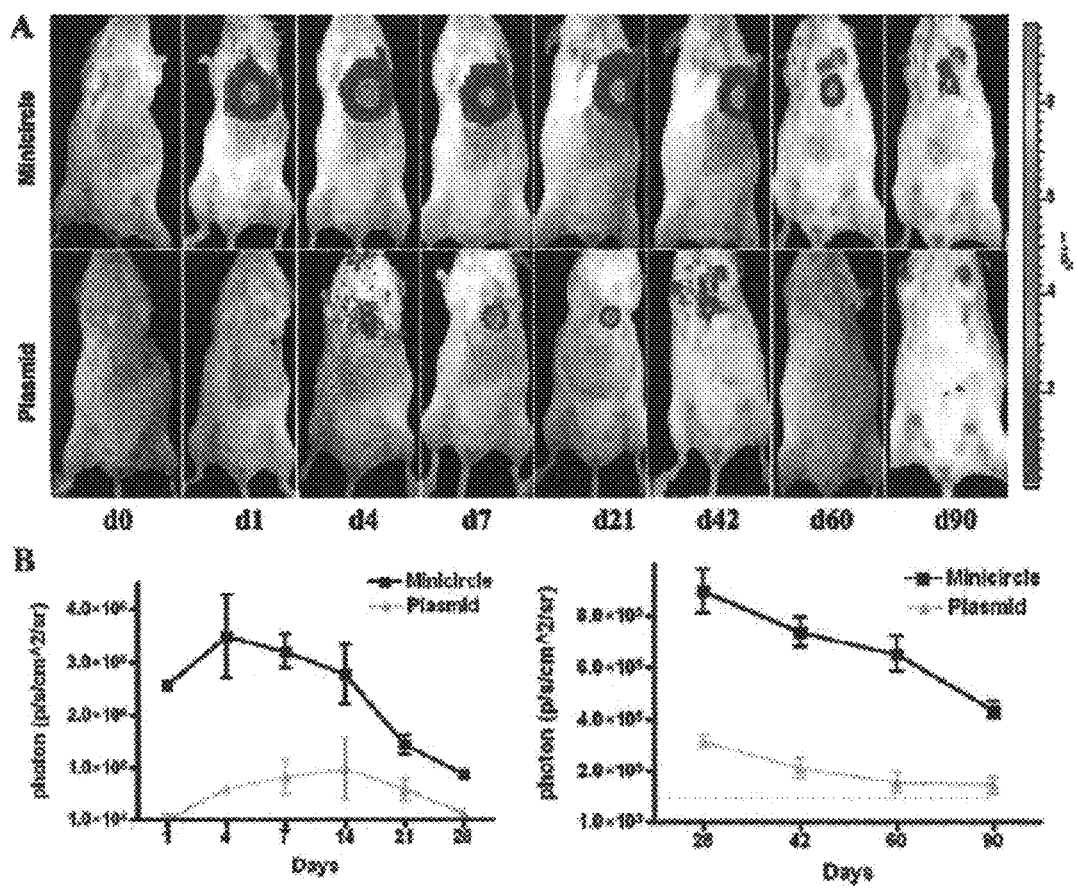
FIG. 9: Comparison of minicircles vs. regular plasmids in vivo. (A) Both MC-DF and PL-DF were injected into normal murine hearts. Mice injected with minicircles (top row) showed more robust Fluc signals compared to mice injected with regular plasmid (bottom row). Transgene expression was detectable at day 1, peaked at week 1-2, and lasted for >90 days. (B) Detailed quantitative analysis of Fluc bioluminescence signals from days 1-28 (left) and days 28-90 (right). Note the difference in Y-axis scale bars (as $p/sec/cm^2/sr$) between the two plots. Background bioluminescence signal is denoted by the dashed line ($1.33×10^4 p/sec/cm^2/sr$).
Figure 10:
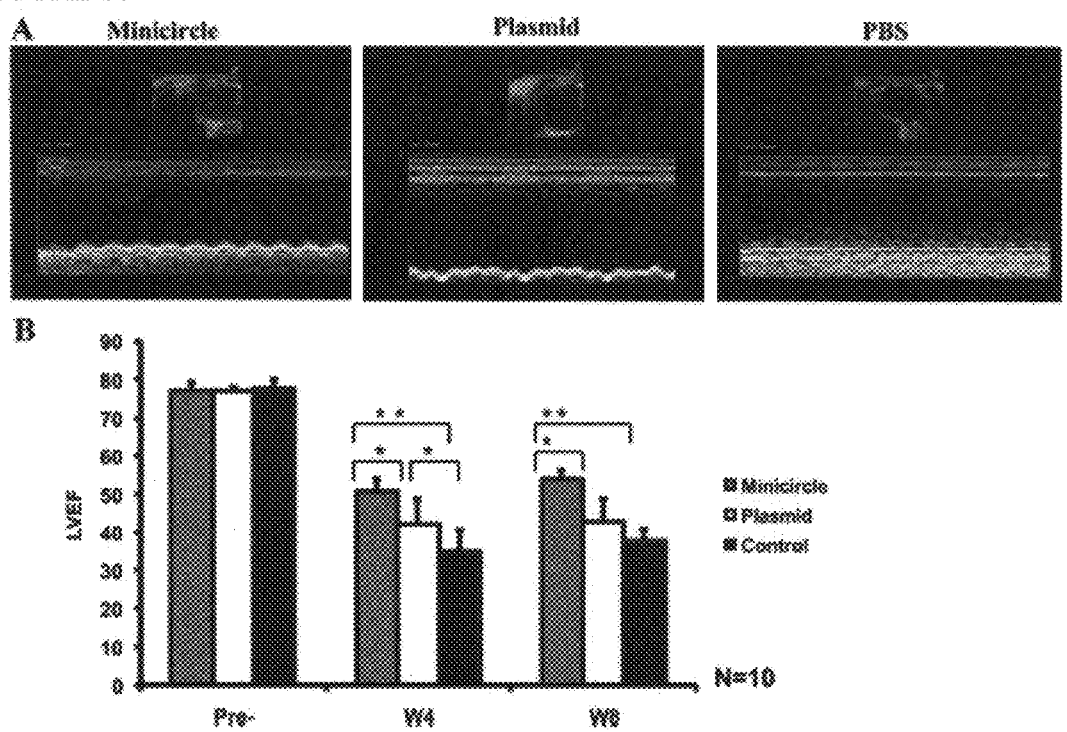
FIG. 10: Evaluation of cardiac function following minicircle vs. plasmid mediated HIF-1α therapy. (A) Representative echocardiogram (M-mode) of mice with LAD ligation following injection of minicircles (left), regular plasmid (middle), or PBS (right) as control group at week 8. (B) Quantitative analysis of left ventricular ejection fraction (LVEF) among the three groups. Compared to saline injection, animals injected with MC-HIF-1α had significant improvements in LVEF at week 4 and week 8. Animals injected with regular plasmids had significant improvement in LVEF at week 4 but not by week 8.

Comparison of novel minicircles vs. regular plasmids in living animals. To determine expression level in vivo, we next injected MC-DF and PL-DF into normal mouse hearts and followed their gene expression from day 0 to day 90 using BLI (FIG. 9A). Quantitative analyses of Fluc activities for both groups are shown in FIG. 3B. Overall, mice injected with MC-DF had significantly higher Fluc activity compared to mice injected with PL-DF at day 1 ($2.6\times10^6\pm7.9\times10^3$ vs. $1.4\times10^4\pm1.3\times10^3$, P<0.001), day 7 ($3.2\times10^6\pm1.5\times10^4$ vs. $6.79\times10^5\pm4.2\times10^3$, P<0.0001), day 14 ($2.8\times10^6\pm2.6\times10^4$ vs. $9.7\times10^5\pm8.6\times10^3$, P<0.0001), day 28 ($8.9\times10^5\pm4.1\times10^3$ vs. $1.6\times10^5\pm3.9\times10^3$, P<0.001), day 42 ($7.4\times10^5\pm8.7\times10^3$ vs. $1.3\times10^5\pm2.9\times10^3$, P<0.0001), day 60 ($6.5\times10^5\pm5.7\times10^3$ vs. $1.3\times10^5\pm3.8\times10^3$, P<0.0001), and day 90 ($4.4\times10^5\pm2.1\times10^3$ vs. $1.45\times10^4\pm3.1\times10^2$ p/s/cm$^2$/sr, P<0.0001). Overall, these data demonstrate minicircles can mediate stronger and longer transgene expression in vivo than regular plasmids.

Figure 4:
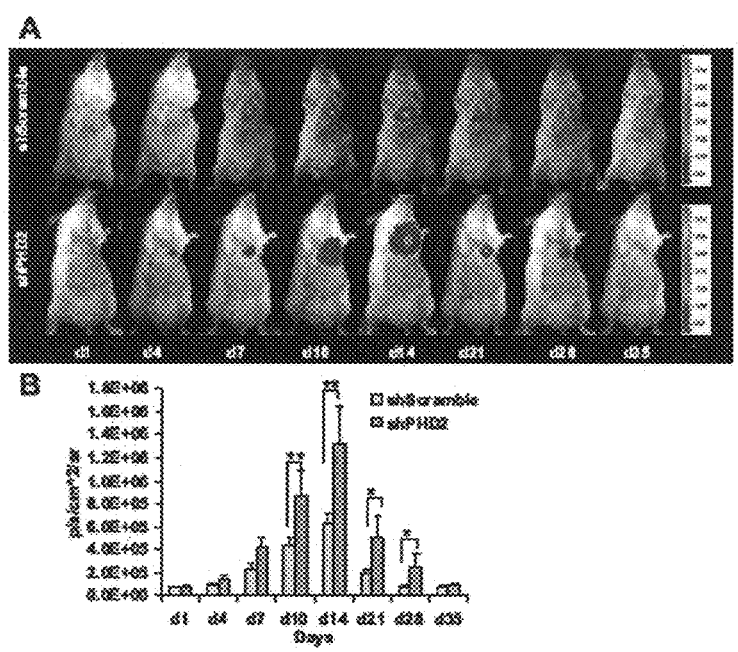
FIG. 4: Molecular imaging of shRNA plasmid fate after intramyocardial delivery. (a) Following myocardial infarction, activation of HIF-1α protein binds to 5×HRE site to activate Fluc expression. Infarcted mice injected with shPHD2 (bottom row) had more robust Fluc signals compared to infarcted mice injected with shScramble (top row) due to knocking down of PHD2, which result in more HIF-1α protein binding to 5×HRE site. Peak transgene expression occurred within week 1-2 as reflected by the Fluc imaging signals. (b) Detailed quantitative analysis of Fluc bioluminescence signals from all animals injected with shPHD2 or shScramble plasmid with LAD ligation. Signal activity is expressed as $p/sec/cm^2/sr$.

Injection of minicircles carrying HIF-1α improved cardiac function following MI. To examine whether using MC-HIF-1α can also improve cardiac function following myocardial infarction, echocardiography was performed before (day −7)

and after (week 2, week 4, and week 8) the LAD ligation. At day −7, the LVEF was comparable in all three groups (FIG. 4). Following LAD ligation, the minicircle group had significantly higher ejection fraction compared to the PBS control group at both week 4 and week 8 ($P<0.01$ for both). The regular plasmid group had significantly higher ejection fraction compared to the PBS group at week 4 (plasmid: 42.2±6.7% vs. PBS: 35.1±5.5%, $P=0.004$). However, this beneficial effect was no longer present by week 8 (42.8±6.0% vs. 37.8±3.4%; $P=0.38$). This is likely due to the short-term transgene expression of regular plasmids (<4 weeks) as shown by our imaging results (FIG. 9A).

Figure 11:
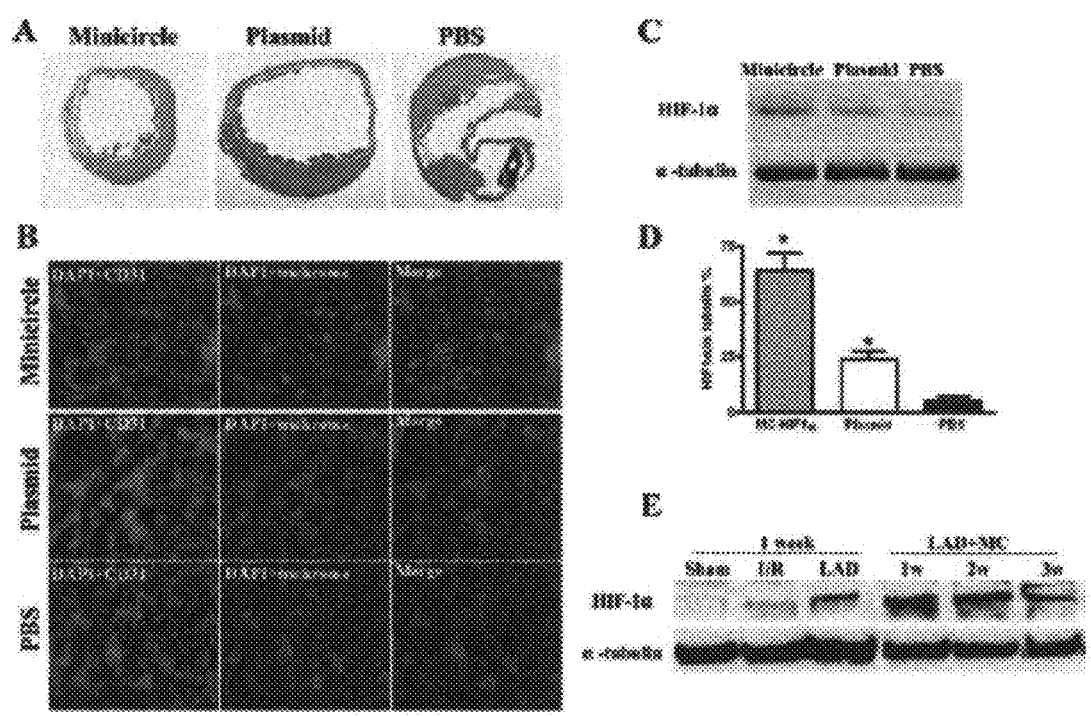
FIG. 11: Confirmation of HIF-1α overexpression in postmortem explanted hearts. (A)

Ex vivo histological validation of in vivo imaging data. After imaging, all animals were sacrificed and hearts explanted. H&E staining showed thicker heart wall size for the minicircle group compared to regular plasmid group and saline group at week 4, confirming the positive functional imaging data seen in echocardiography (FIG. 11A). Minicircle treatment significantly decreased left ventricular scarring compared to plasmids and PBS control (12.8±1.3% vs. 21.5±3.5% vs. 31.2±3.6%; $P<0.05$ MC vs PL; $P<0.01$ MC vs. PBS). Immunohistochemistry of the peri-infarct region by CD31 staining also showed increased neovascularization in the minicircle (389±73) compared to the regular plasmid (251±21) and PBS (138±10 vessels/mm$^2$) groups ($P<0.05$ for both) (FIG. 11B). To further confirm the in vivo functional imaging data, we assayed for HIF-1α protein expression of explanted hearts at day 14. Quantitative analysis of the Western blot indicates that HIF-1α proteins were significantly higher in the minicircle-treated hearts compared to regular plasmids and PBS-treated hearts (FIG. 11C-D). Finally, we also investigated HIF-1α expression levels in different ischemia conditions as well as in different time point after LAD ligation. Western blot data show that endogenous HIF-1α is most robust following LAD ligation compared to ischemia-reperfusion and sham surgery, suggesting that activation of endogenous HIF-1α expression level is directly related to the size of MI (FIG. 11E). With co-administration of MC-HIF-1α, highest levels of HIF-1α are detected at week 1. The levels of MC-treated HIF-1α decreases at subsequent week 2 and week 3, similar to the in vivo imaging pattern that was observed for Fluc transgene expression in FIG. 3A.

Comparison of viral vs. non-viral vectors in FVB mice. Adenoviral vectors carrying either VEGF or FGF have been used for several cardiac gene therapy trials. However, our group has previously shown that repeated injection of adenovirus induces a significant host cellular and humoral immune response. Recently, AAV has generated significant interest as a safer and more effective vehicle for cardiac gene transfer. Indeed, AAV carrying sacroplasmic reticulum calcium ATPase (SERCA2a) has been used for treatment of patients with heart failure delivering. Here we investigated the duration of gene expression after repeated intramuscular transplantation of AAV vs. minicircle and regular plasmid into immunocompetent adult female FVB mice (n=5 per group). FIG. 12 shows that AAV-mediated Fluc expression was significantly higher compared to MC and PL after first injection as expected. At day 7, the activities were 1.42× 10$^7$±8.65×10$^5$ vs. 7.46×10$^6$±5.52×10$^5$ vs. 2.85×10$^5$±9.46×10$^4$ p/s/cm$^2$/sr for each group, respectively ($P<0.05$ AAV vs. MC and $P<0.001$ AAV vs. PL). At day 28, the activities were 2.31×10$^6$±6.3×10$^5$ vs. 3.34×10$^5$±7.25×10$^4$ vs. 1.88×10$^4$±3.51×10$^4$ p/s/cm$^2$/sr, respectively ($P<0.05$ AAV vs. MC and $P<0.001$ AAV vs. PL). However, repeat administration of AAV in the contralateral leg at 4 weeks after primary injection resulted in no AAV-mediated signal expression. At day 28, the BLI signals for MC were comparable between first and second injection (3.34×10$^5$±7.25×10$^4$ vs. 2.15×10$^5$±3.83×10$^4$; $P=NS$) whereas the BLI signals for AAV were significantly reduced (2.31×10$^6$±6.31×10$^5$ vs. 1.12×10$^4$±6.46×10$^3$ p/s/cm$^2$/sr; $P<0.0001$). Taken together, these data suggest that AAV is capable of triggering both cellular and humoral immune response, which are consistent with two previous reports of dose-dependent generation of CD8$^+$ T-cell responses to AAV capsid proteins in humans trials for treatment of hemophilia and type 1 hypertriglyceridemia deficiency.

Discussion

Shown herein are methods using a novel non-viral vector carrying a robust therapeutic gene and validating the results with molecular imaging technology. The major findings are the following: (1) Minicircles can be easily isolated from the bacterial culture. In our study, we used parental plasmids encoding the inducible φc31 recombinase and ISce1 enzyme and its restriction, together with a transgene flanked with the attB and attP sites, site, to obtain large amounts of purified minicircles. (2) Minicircles show earlier onset and more robust transgene expression than conventional plasmids both in vitro and in vivo. In particular, flow cytometry data showed significant eGFP positivity by 12 hr compared to normal plasmids. BLI shows that MC-DF injected into murine hearts lasted >90 days, much longer than the 28 days seen in regular plasmids. (3) Direct injections of MC-HIF-1α can improve ventricular function and enhance neoangiogenesis in a mouse model of myocardial infarction for 8 weeks, compared to 4 weeks for regular plasmids. (4) Lastly, repeated injections of MC have comparable transgene activities. In contrast, repeated injections of AAV lead to significant reduction of transgene expression due to host cellular and humoral immune response.

Non-viral vectors have many advantages over viral systems: a better safety profile, the absence of theoretical size limitation for the expression cassette, and possibly simpler clinical translation due to easier good manufacturing practices (GMP). On the other hand, concerns have been raised regarding (1) the lack of robust transfection efficiency and (2) the immunostimulatory prokaryotic CpG motives in the bacterial backbone. To resolve these issues, we designed the novel non-viral minicircle plasmids which exhibited up to eight-fold higher gene expression than the regular plasmid in vitro as well significantly longer transgene expression in vivo. This drastic improvement is due to the removal of unnecessary plasmid sequences, which could affect the gene expression, and the smaller size of the minicircles which might confer better extracellular and intracellular bioavailability and thus improved gene delivery properties. In particular, the bacterial backbone sequences are often abundant with CpG islands, which can lead to transcriptional gene silence and, when mixed with lipid, trigger immune responses to kill the cells that harbor the DNA-lipid mix in vivo, and is one of the major reasons why regular plasmids are notoriously ineffective for long-term expression.

The HIF-1 complex is known to control the expression of over 60 genes that affect cell survival and metabolism in adverse conditions. As an upstream transcriptional factor, HIF-1α is involved in activation of several pathways. Overexpression of HIF-1α has critical functional consequences, including an improvement in neoangiogenesis due to upregulation of VEGF, FGF, and eNOS. Importantly, recent evidence suggests that the expression of a single angiogenic factor such as VEGF alone may not be sufficient for the functional revascularization of ischemic tissues. Thus, newer approaches based on upregulation of the master regulator HIF-1α may be a more potent choice. In this study, we selected HIF-1α as a therapy target gene, which resulted in significant functional improvements after delivery into the infarcted hearts. Immunohistological results demonstrated that higher HIF-1α expression led to formation of more small vessels which in turn improved cardiac function.

In summary, minicircles are novel non-viral vectors that lack an origin of replication and an antibiotic selection marker, and carry only short bacterial sequences. Our results suggest that using minicircles to deliver HIF-1α may represent a potentially new therapeutic target in the field of cardiovascular gene therapy.

Example 4

Overexpression of HIF-1-Alfa Utilizing Non-Viral 'Minicircle' Gene Therapy Improves Neovascularization in Peripheral Artery Disease Hypoxia Inducible Factor-1-Alfa (HIF-1-Alfa) promotes (neo)angiogenesis in ischemic tissue by regulating over 60 genes including VEGF and FGF. Short hairpin RNA interference targeting PHD2 (shPHD2) prevents HIF-1-Alfa degradation. Here we studied the effect of shPHD2 injection on neovascularization in a mouse hind limb ischemia model. We compared the use of the recently developed Minicircle (MC) vector with the conventional Plasmid (PL) vector.

Methods:

The in vitro kinetics of MC incorporation were compared with PL incorporation kinetics by measuring Bioluminescence imaging (BLI) signals after firefly Luciferase (Fluc) transfection of mouse C2C12 myoblast cells. The cells were transfected with 2 ug of MC-Fluc or equimolar 4 ug of PL-Fluc using Lipofectamine 2000 (Invitrogen) according to the manufacturer's protocol. BLI was performed with the Xenogen In Vivo Imaging System (Alameda, Calif.) and the signals were quantified in maximum photons per second per centimeter squared per steradian (p/s/cm2/sr). BLI was performed on time points 3, 24 and 48 hours after transfection.

To compare the in vivo gene expression, 8-10 weeks old C57/B6 mice (n=3) were intramuscularly (gastrocnemic muscle) injected with MC-Fluc, or with a contralateral injection of PL-Fluc. BLI was measured on day 1, 3, 5, 7 and weekly up to 4 weeks after injection.

On additional C57/B6 mice (n=48) a unilateral femoral artery ligation was performed by coagulation of the left femoral artery proximal to the bifurcation of deep and superficial femoral artery with an additional coagulation of the distal femoral artery. The mice were randomized into 3 groups: 12.5 ug MC-shPHD2 injection group; an equimolar 25 ug PL-shPHD2 injection group; and a PBS injection group as a negative control.

Laser Doppler perfusion imaging (LDPI, Moor instruments) was performed to analyze the blood flow in the paws. The LDPI system incorporates a helium-neon laser generating a beam of light that scans a 12×12 cm tissue surface, measuring the shift of frequency of incident light according to the Doppler principle. This shift of frequency is caused by the blood cells moving through the vasculature. The calculated perfusion was expressed as a ratio of left (ischemic) to right (normal) limb, to account for variables such as ambient light and temperature. LDPI measurements were done pre-operatively and on day 0; 3; 5; 7; 14; 21 and 28. On day 7 and day 21, 3 mice were euthanized for gastrocnemius HIF-1-Alfa expression Western Blot analysis.

Statistics were calculated using SPSS 16.0 (SPSS Inc). Descriptive statistics included mean and standard error. Comparison between groups was performed using non-parametric Mann-Whitney U tests. Differences were considered significant at p≦0.05.

Results:

MC transfection showed to be more efficient than PL transfection, in vitro, with a BLI signal at 48 hours of $2.8 \cdot 10^6 \pm 2.5 \cdot 10^5$ and $6.5 \cdot 10^5 \pm 6.9 \cdot 10^3$ (p<0.05), respectively. Long term in vivo analysis of the MC-Fluc and PL-Fluc transfection showed a more efficient MC-Fluc transfection on day 28 compared to PL-Fluc transfection with BLI signals of $2.0 \cdot 10^4 \pm 1.7 \cdot 10^4$ en $2.74 \cdot 10^3 \pm 1.1 \cdot 10^3$ respectively (p=0.05).

Laser Doppler measurements showed a significantly improved blood flow recovery in the MC-shPHD2 injection group in comparison to the PBS injection group, up to 14 days after femoral artery ligation, with LDPI perfusion ratios of 0.82±0.085 and 0.58±0.084, respectively (p<0.05). At that time point, a trend towards improved blood flow recovery was seen in the PL-Fluc group: 0.67±0.074 (p=ns). MC-shPHD2 injection resulted in a significant improvement of initial blood flow recovery compared to PL-shPHD2 injection, with LDPI perfusion ratios of 0.55±0.079 and 0.33±0.064 respectively on day 7 (p<0.05, see FIG. 1).

Western blot analysis showed higher expression levels of HIF-1-alfa in the MC-shPHD2 group of 0.53±0.051, compared to 0.26±0.023 in the PBS group at 3 weeks (p<0.05).

Conclusion:

Through the HIF-1-Alfa pathway, shPHD2 gene therapy improves blood flow recovery in this murine model of hind limb ischemia, with significant advantages of minicircle as a vector. The combination MC-shPHD2 is a promising new form of gene therapy for the treatment of patients with limb ischemia caused by peripheral artery disease.

Example 3

HIF-1 is a master regulator which activates more than 60 genes including VEGF and FGF. PHD is a negative regulator of HIF-1 and hence inhibition of PHD can induce HIF-1. We have used minicircle vector to express short hairpin PHD2 (shPHD2) in porcine myocardial infarction (MI) model to assess the efficacy of shPHD2 for improving cardiac function.

Minicircle preparation was performed following the protocol previously described by Chen and coworkers (Chen et al., 2005). A total of 5 pigs weighing 45-60 kg were tested with 5 mg of minicircles injection each. Pigs were sedated with ketamine hydrochloride (20 mg/kg, intramuscularly) and anesthetized with a bolus infusion of thiopental sodium (5.0-7.0 mg/kg intravenously), followed by endotracheal intubation. General endotracheal anesthesia was established with 3.0% isoflurane at the beginning of the surgical preparation, and maintained with 1.0% throughout the experiment. The LAD coronary artery was occluded 3 mm distal to the origin of the second diagonal branch. Myocardial ischemia was confirmed visually by regional cyanosis of the myocardial surface.

40 injections of 100 μl volume of minicircles (5 mg total) were performed near the peri-infarction area with 1-mL syringes and 27-gauge needles. Control pigs received MI+normal saline (NS) injection instead. Sham pigs underwent lateral thoracotomy but no induction of MI. Four weeks after minicircle injection, cardiac echocardiography was performed to evaluate heart function (see FIG. 14). Results demonstrate a strong trend toward improvement of cardiac function following minicircle-shPHD2 therapy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for treatment of ischemic coronary artery disease in a patient, the method comprising:
administering by local delivery an effective dose of a minicircle DNA vector comprising polynucleotide sequences that potentiate HIF-1 activity by inhibiting expression of at least one protein that hydroxylates HIF-1 to said patient, for a time and in an amount sufficient to stably and efficiently transduce cardiomyocytes involved in said ischemic coronary artery disease, wherein said administering provides for increased angiogenesis.

2. The method of claim 1, wherein the polynucleotide sequences inhibit expression through an RNAi mechanism.

3. The method of claim 2, wherein the nucleotide sequences encode an shRNA specific for prolyl hydroxylase.

4. A method for treatment of ischemic coronary artery disease (CAD) in a patient, the method comprising:
administering intramyocardially an effective dose to said patient of a minicircle DNA vector comprising polynucleotide sequences that potentiate HIF-1 activity by inhibition through an RNAi mechanism of prolyl hydroxylase wherein the prolyl hydroxylase is PHD2, for a time and in an amount sufficient to stably and efficiently transduce cardiomyocytes involved in said ischemic cardiovascular disease, wherein said administering provides for increased angiogenesis.

5. The method of claim 1, wherein the minicircle DNA vector is delivered intramyocardially.

6. The method of claim 5, wherein the minicircle DNA vector is delivered at multiple sites of the heart.

7. The method of claim 1, wherein said patient is an animal model for CAD.

8. The method of claim 1, wherein the patient is a human.

9. The method of claim 1, wherein the patient is suffering from cardiac ischemia.

10. The method of claim 1, wherein the protein that hydroxylates HIF-1 is a prolyl hydroxylase.

11. The method of claim 1, wherein the protein that hydroxylates HIF-1 is factor inhibiting HIF-1 (AsPHD).

12. The method of claim 1, wherein the minicircle comprises polynucleotide sequences that inhibit expression by an RNAi mechanism of PHD2 and AsPHD.

* * * * *